United States Patent [19]

Williams et al.

[11] Patent Number: 5,750,867
[45] Date of Patent: May 12, 1998

[54] MAINTENANCE OF MALE-STERILE PLANTS

[75] Inventors: Mark Williams; Jan Leemans, both of Ghent, Belgium

[73] Assignee: Plant Genetic Systems, N.V., Brussels, Belgium

[21] Appl. No.: 351,413

[22] PCT Filed: Jun. 11, 1993

[86] PCT No.: PCT/EP93/01489

§ 371 Date: Feb. 8, 1995

§ 102(e) Date: Feb. 8, 1995

[87] PCT Pub. No.: WO93/25695

PCT Pub. Date: Dec. 23, 1993

Related U.S. Application Data

[63] Continuation of Ser. No. 970,849, Nov. 3, 1992, abandoned, which is a continuation of Ser. No. 899,072, Jun. 12, 1992, abandoned.

[51] Int. Cl.$^6$ .............................. A01H 5/00; A01H 1/02; C12N 15/29; C12N 15/55; C12N 15/82
[52] U.S. Cl. .............................. 800/205; 800/DIG. 56; 800/250; 435/172.3; 435/199; 435/418; 435/419; 536/23.2; 536/23.6; 536/23.7; 536/24.1; 47/58; 47/DIG. 1
[58] Field of Search .............................. 435/240.4, 320.1, 435/172.3, 199, 418, 419; 47/58, DIG. 1; 800/205, 250, DIG. 56; 536/23.2, 23.7, 23.6, 24.1

[56] References Cited

U.S. PATENT DOCUMENTS

| | | | |
|---|---|---|---|
| 3,710,511 | 1/1973 | Patterson | 47/58 |
| 3,861,079 | 1/1975 | Patterson | 47/58 |
| 4,658,084 | 4/1987 | Beversdorf et al. | 800/200 |
| 4,727,219 | 2/1988 | Brar et al. | 800/800 |
| 5,356,799 | 10/1994 | Fabijanski et al. | 435/172.3 |
| 5,478,369 | 12/1995 | Albertsen et al. | 47/58 |

FOREIGN PATENT DOCUMENTS

| | | |
|---|---|---|
| 0344029 | 11/1989 | European Pat. Off. . |
| 0412911 | 2/1991 | European Pat. Off. . |
| WO 9008828 | 8/1990 | WIPO . |

OTHER PUBLICATIONS

Mariani et al. (1992) Nature vol. 357: pp. 384–387, Jun. 4, 1992.

Hartley (1988) J. Mol. Biol. vol. 202: pp. 913–915, 1988.

Aarts et al., Nature, vol. 363 (1993), pp. 715–717.

Zabaleta et al., Proc. Natl. Acad. Sci. USA, vol. 93, (1996) pp. 11259–11263.

Stoskopf et al., Plant Breeding Theory and Practice, (1993), Cell and Molecular Biology Tools for Plant Breeding, Chapter 22, pp. 453–472.

Poehlman, Breeding Field Crops, Third Edition, Hybird Corn, pp. 473–476 (1987).

Sprague, Production of Hybrid Seed, American Society of Agronomy, Inc. (1977), pp. 685–693.

*Primary Examiner*—David T. Fox
*Attorney, Agent, or Firm*—Birch, Stewart, Kolasch & Birch, LLP

[57] ABSTRACT

Transgenic plants that have, stably integrated into their nuclear genome, a maintainer gene comprising a fertility-restorer gene and a pollen-lethality gene. The plants can be used to maintain a homogeneous population of male-sterile plants.

33 Claims, No Drawings

MAINTENANCE OF MALE-STERILE PLANTS

This application is the national phase application from PCT International Application Number PCT/EP93/01489 filed on 11 Jun. 1993 and claims priority thereon pursuant to 35 U.S.C. § 371. This application is a continuation of U.S. application Ser. No. 07/970,849 filed Nov. 3, 1992, now Abandoned, which is a continuation of U.S. application Ser. No. 08/899,072 filed on Jun. 12, 1992 now abandoned.

FIELD OF THE INVENTION

This invention relates to a process for maintaining male-sterile plant lines that can be used for the production of hybrid seed of a crop, to maintainer plants that can be used in such a process, and to maintainer genes that can be used to produce such maintainer plants.

BACKGROUND OF THE INVENTION

In many, if not most, plant species, the development of hybrid cultivars is highly desired because of their generally increased productivity due to heterosis: the superior performance of hybrid individuals compared with their parents (see, e.g., Fehr (1987) "Principles of Cultivar Development, Volume 1: Theory and Technique", MacMillan Publishing Company, New York; Allard (1960) "Principles of Plant Breeding", John Wiley and Sons, Inc., New York).

The development of hybrid cultivars of various plant species depends upon the capability to achieve almost complete cross-pollination between parents. This is most simply achieved by rendering one of the parent lines male-sterile (i.e., with pollen being absent or nonfunctional), for example, by manually removing the one parent's anthers or by providing the one parent with naturally occurring cytoplasmic or nuclear genes that prevent anther and/or pollen development and/or function, using classical breeding techniques (for a review of the genetics of male-sterility in plants, see Kaul (1988) "Male Sterility in Higher Plants", Springer Verlag, New York).

For hybrid plants where the seed is the harvested product (e.g., corn and oilseed rape), it is, in most cases, also necessary to ensure that fertility of the hybrid plants is fully restored. In plants in which the male-sterility is under genetic control, this requires the use of genes that can restore male-fertility. Hence, the development of hybrid cultivars is mainly dependent on the availability of suitable and effective sterility and restorer genes.

Endogenous nuclear loci are known for most plant species that contain genotypes which effect male-sterility, and generally, such loci need to be homozygous for particular recessive alleles in order to result in a male-sterile phenotype. The presence of a dominant male-fertile allele at such loci results in male-fertility.

Recently, it has been shown that male-sterility can be induced in a plant by providing the plant with a nuclear male-sterility genotype that includes a chimaeric male-sterility gene comprising a DNA sequence (or male-sterility DNA) coding, for example, for a cytotoxic product (such as an RNase) and under the control of a promoter which is predominantly active in selected tissue of the plant's male reproductive organs. In this regard, tapetum-specific promoters, such as the promoter of the TA29 gene of Nicotiana tabacum, have been shown to be particularly useful for this purpose (Mariani et al (1990) Nature 347:737; European patent publication ("EP") 0,344,029). By providing the nuclear genome of the plant with such a male-sterility gene, an artificial nuclear male-sterility locus is created containing the artificial male-sterility genotype that results in a male-sterile plant.

In addition, it has been recently shown that male-fertility can be restored to such a nuclear male-sterile plant with a chimaeric fertility-restorer gene comprising another DNA sequence (or fertility-restorer DNA) that codes, for example, for a protein that inhibits the activity of the cytotoxic product or otherwise prevents the cytotoxic product from being active at least in the selected tissue of the plant's male reproductive organs (EP 0,412,911). For example, the barnase gene of Bacillus amyloliguefaciens codes for an RNase (Barnase) which can be inhibited by a protein (Barstar) that is encoded by the barstar gene of B. amyloliguefaciens. Hence, the barnase gene can be used for the construction of a chimaeric male-sterility gene while the barstar gene can be used for the construction of a chimaeric fertility-restorer gene. Experiments in different plant species (e.g., oilseed rape) have shown that such a chimaeric barstar gene can fully restore the male-fertility of male-sterile lines in which the male-sterility was due to the presence of a chimaeric barnase gene (EP 0,412,911: Mariani et al (1991) Proceedings of the CCIRC Rapeseed Congress, July 9–11, 1991 Saskatoon, Saskatchewan, Canada; Mariani et al (1992) Nature 357:384). By coupling a marker gene, such as a dominant herbicide resistance gene (for example, the bar gene coding for phosphinothricin acetyl transferase (PAT) that converts herbicidal phosphinothricin to a non-toxic compound [De Block et al (1987) EMBO J. 6:2513]), to the chimaeric male-sterility and/or fertility restorer gene, breeding systems can be implemented to select for uniform populations of male-sterile plants (EP 0,344,029; EP 0,412,911).

The production of hybrid seed of any particular cultivar of a plant species requires the: 1) maintenance of small quantities of pure seed of each inbred parent; and 2) the preparation of larger quantities of seed of each inbred parent. Such larger quantities of seed would normally be obtained by several (usually two) seed-multiplication rounds, starting from a small quantity of pure seed ("basic seed") and leading, in each multiplication round, to a larger quantity of seed of the inbred parent and finally to a stock of seed of the inbred parent ("parent seed" or "foundation seed") which is of sufficient quantity to be planted to produce the desired quantities of hybrid seed. Of course, in each seed-multiplication round, larger planting areas (fields) are required.

In order to maintain and enlarge a small stock of seeds of male-sterile plants, it has been necessary to cross the parent male-sterile plants with normal pollen-producing parent plants. The offspring of such a cross will, in all cases, be a mixture of male-sterile and male-fertile plants, and the latter have to be removed from the former. With male-sterile plants containing an artificial male-sterility locus as described above, such removal can be facilitated by genetically linking the chimaeric male-sterility gene to a suitable marker gene, such as the bar gene, which allows the easy identification and removal of the male-fertile plants. EP 0,198,288 and U.S. Pat. No. 4,717,219, by comparison, describe methods for linking such marker genes (which can be visible markers or dominant conditional markers) to endogenous nuclear loci containing male-sterility genotypes.

However, even when suitable marker genes are linked to male-sterility genotypes, the maintenance of parent male-sterile plants still requires the removal from the field of a substantial number of plants. For instance, in systems using a herbicide resistance gene (e.g., the bar gene) linked to a chimaeric male-sterility gene, only half of the parent stock will result in male-sterile plants, thus requiring the removal of the male-fertile plants by herbicide spraying prior to flowering. In any given field, the removal of male-fertile plants effectively reduces the potential yield of hybrid seed or the potential yield of male-sterile plants during each round of seed multiplication for producing of parent seed. This is economically unattractive for many important crop species such as corn and oilseed rape. In order to minimize the number of male-fertile plants which have to be removed, male-fertile maintainer plants have been sought which, when crossed with a male-sterile parent plant, produce a minimum, preferably no, male-fertile offspring, thereby minimizing or avoiding altogether the need to remove such male-fertile offspring. To solve an analogous problem, U.S. Pat. Nos. 3,710,511 and 3,861,079 have described procedures for producing and maintaining a homogenous population of male-sterile plants by using specific chromosomal abnormalities that are differentially transmitted to the egg and the sperm in the plants.

SUMMARY OF THE INVENTION

In accordance with this invention, a cell of a transgenic plant ("the maintainer plant") is provided, in which the nuclear genome contains stably integrated therein: 1) at a first locus or male-sterility locus, a male-sterility genotype in homozygous condition; and 2) at a second locus or maintainer locus, a maintainer gene in heterozygous condition; the male-sterility locus and the maintainer locus preferably being unlinked; the maintainer gene being a foreign DNA sequence, preferably a foreign chimaeric DNA sequence, containing:

a) a fertility-restorer gene that comprises at least:
  i) a fertility-restorer DNA encoding a restorer RNA and/or protein or polypeptide which, when produced or overproduced in some or all of the cells, preferably stamen cells, of the plant, prevents phenotypic expression of the nuclear male-sterility genotype that would render the plant male-sterile in the absence of expression of the fertility-restorer DNA in some or all stamen cells; and
  ii) a restorer promoter capable of directing expression of the fertility-restorer DNA at least in some or all of the cells, preferably stamen cells, of the plant, so that the phenotypic expression of the nuclear male-sterility genotype is prevented, the fertility-restorer DNA being in the same transcriptional unit as, and under the control of, the restorer promoter and b) a pollen-lethality gene that is selectively expressed in microspores and/or pollen of the plant to produce nonfunctional pollen and that comprises at least:
  iii) a pollen-lethality DNA coding for a pollen-lethality RNA and/or protein or polypeptide that, when produced or overproduced in the microspores and/or pollen, significantly disrupts their metabolism, functioning and/or development; and
  iv) a pollen-specific promoter capable of directing expression of the pollen-lethality DNA selectively in the microspores and/or pollen of the plant, the pollen-lethality DNA being in the same transcriptional unit as, and under the control of, the pollen promoter.

The cell of the maintainer plant of this invention preferably also comprises, especially in the maintainer locus, at least one first marker gene which comprises at least:

v) a first marker DNA encoding a first marker RNA and/or protein or polypeptide which, when present at least in a first specific tissue or specific cells of the plant, renders the plant easily separable from other plants which do not contain the first marker RNA, protein or polypeptide encoded by the first marker DNA at least in the first specific tissue or specific cells; and vi) a first marker promoter capable of directing expression of the first marker DNA at least in the first specific tissue or specific cells, the first marker DNA being in the same transcriptional unit as, and under the control of, the first marker promoter.

The male-sterility genotype in the cell of the maintainer plant of this invention can be foreign or endogenous but is preferably a foreign, especially chimaeric, male-sterility gene which comprises:

1) a male-sterility DNA encoding a sterility RNA and/or protein or polypeptide which, when produced or overproduced in a stamen cell of the plant in the absence of the restorer RNA, protein or polypeptide, significantly disturbs the metabolism, functioning and/or development of the stamen cell; and 2) a sterility promoter capable of directing expression of the male-sterility DNA selectively in stamen cells of the plant, the male-sterility DNA being in the same transcriptional unit as, and under the control of, the sterility promoter.

The male-sterility genotype in the maintainer plant cell of this invention preferably comprises, especially in the male-sterility locus, at least one second marker gene which comprises at least:

3) a second marker DNA encoding a second marker RNA and/or protein or polypeptide which, when present at least in the second specific tissue or specific cells of the plant, renders the plant easily separable from other plants which do not contain the second marker RNA, protein or polypeptide encoded by the second marker DNA at least in the second specific tissue or specific cells; and 4) a second marker promoter capable of directing expression of the second marker DNA at least in the second specific tissue or specific cells, the second marker DNA being in the same transcriptional unit as, and under the control of, the second marker promoter.

Also in accordance with this invention are provided maintainer plants, the seeds of such plants, and plant cell cultures, all of which consist essentially of the cells of this invention.

Further in accordance with this invention are provided the maintainer gene and plasmids containing the maintainer gene, as well as bacterial host cells (e.g., E. coli or Agrobacterium) containing such plasmids.

Still further in accordance with this invention is provided a process for producing, preferably enlarging, a homogeneous population of male-sterile plants and their seed that contain a nuclear male-sterility gene in homozygous condition, the process comprising the step of crossing the male-sterile plants with the maintainer plants of this invention. The seed from the resulting male-sterile plants can be harvested and grown into the male-sterile plants. Hybrid seed can then be produced by crossing the male-sterile plants with male-fertile plants of another inbred parent line used as pollinators.

Yet further in accordance with this invention is provided a process for producing, preferably enlarging, a population of the maintainer plants, comprising the step of selfing the maintainer plants.

BRIEF DESCRIPTION OF THE TABLE

Table 1 describes a ten step procedure to obtain corn (e.g., H99) maintainer plants according to the present invention.

DETAILED DESCRIPTION OF THE INVENTION

A male-sterile plant of this invention is a plant of a given species with a nuclear male-sterility genotype.

A restorer plant of this invention is a plant of the same plant species containing, within its nuclear genome, a fertility-restorer gene that is able to restore the male-fertility in offspring which are obtained from a cross between the male-sterile plant and the restorer plant and which contain both the male-sterility genotype and the fertility-restorer gene.

A restored plant of this invention is a plant of the same species that is male-fertile and that contains, within its nuclear genome, the male-sterility genotype and the fertility-restorer gene.

A parent plant or parent of this invention is a plant that can be used for the production of hybrid seed. The female or seed parent plant is the parent from which the hybrid seed is harvested. For the purposes of this invention, the female parent will always be a male-sterile plant. The male or pollen parent is the parent that is used to fertilize the female parent. In many cases, the male parent will also be a restorer plant.

A line is the progeny of a given individual plant.

The male-sterility genotype of this invention is the genotype of at least one locus, preferably only one locus, in the nuclear genome of a plant (i.e., the male-sterility locus), the allelic composition of which can result in male-sterility in the plant. A male-sterility genotype can be endogenous to the plant, but it is generally preferred that it be foreign to the plant. Preferred foreign male-sterility genotypes are those in which the allele responsible for male-sterility contains a foreign male-sterility gene that comprises:

1) a male-sterility DNA encoding a sterility RNA and/or protein or polypeptide which, when produced or overproduced in a stamen cell of the plant, significantly disturbs the metabolism, functioning and/or development of the stamen cell; and 2) a sterility promoter capable of directing expression of the male-sterility DNA selectively in stamen cells of the plant, the male-sterility DNA being in the same transcriptional unit as, and under the control of, the sterility promoter.

Such a male-sterility gene is always a dominant allele at a foreign male-sterility locus. The recessive allele corresponds to the absence of the male-sterility gene in the nuclear genome of the plant.

Preferred foreign male-sterility DNAs and sterility promoters that can be used in the male-sterility genes in female parent plants and maintainer plants of this invention have been described in EP 0,344,029. A particularly useful male-sterility DNA codes for Barnase (Hartley (1988) J. Mol. Biol. 202:913). Particularly useful sterility promoters are tapetum-specific promoters such as the promoter of the TA29 gene of *Nicotiana tabacum* (EP 0,344,029) which can be used in tobacco, oilseed rape, lettuce, chicory, corn and other plant species; the PT72, the PT42 and PE1 promoters from rice, the sequences of which are given in SEQ ID no. 7, SEQ ID no. 8, and SEQ ID no. 9, respectively, in the Sequence Listing and which can be used in rice and other plant species (PCT application PCT/EP 92/00274); and the PCA55 promoter from corn, the sequence of which is given in SEQ ID No. 10, which can be used in corn and other plant species (PCT application PCT/EP 92/00275).

A preferred endogenous male-sterility genotype is one in which a recessive allele ("m") in homozygous condition (m/m) at a male-sterility locus produces male-sterility. At a male-sterility locus, male-fertility would otherwise be encoded by a corresponding dominant allele ("M"). Such a male-sterility genotype is known in many plant species (see Kaul (1988) supra; and 1992 issues of Maize Genetics Cooperation Newsletter, published by the Department of Agronomy and U.S. Department of Agriculture, University Of Missouri, Columbia, Mo., U.S.A.). The DNA sequences in the nuclear genome of a plant corresponding to m and M alleles can be identified by gene tagging, i.e., by insertional mutagenesis using transposons, or by means of T-DNA integration (see, e.g., Wienand and Saedler (1987) In "Plant DNA Infectious Agents", Ed. by T. H. Hohn and J. Schell, Springer Verlag, New York, p. 205; Shepherd (1988) In "Plant Molecular Biology: a Practical Approach", IRL Press, p. 187; and Teeri et al (1986) EMBO J. 5:1755).

Fertility-restorer DNAs and restorer promoters that can be used in the maintainer genes of this invention with a foreign male-sterility genotype have been described in EP 0,412,911. In this regard, fertility-restorer genes in which the fertility-restorer DNA encodes Barstar (Hartley (1988) J.Mol. Biol. 202:913) and is under control of tapetum-specific promoters, such as those described above as sterility promoters, are of particular use. In particular, it is believed that a fertility-restorer DNA coding for a mutant of Barstar, in which the cysteine residue at its position 40 is replaced by serine (Hartley (1989) TIBS 14:450), functions better in restoring the fertility in the restored plants of some species.

When an endogenous male-sterility genotype is homozygous for a recessive allele m, it is preferred that the fertility-restorer gene be the dominant allele M of that male-sterility genotype, preferably under the control of its own promoter. The DNA corresponding to such a dominant allele, including its natural promoter, can be isolated from the nuclear genome of the plant by means of gene tagging as described above.

The pollen-lethality DNAs that are used in the pollen-lethality genes of this invention preferably encode an RNA and/or a protein or polypeptide that, when expressed in microspores or pollen, significantly disrupts their metabolism, functioning and/or development. In this regard, the pollen-lethality DNAs can encode RNAs, proteins or polypeptides such as those encoded by the male-sterility DNAs described in EP 0,344,029. Of particular interest are male-sterility DNAs that encode ribonucleases (EP 0,344, 029) such as RNase T1 from *Aspergillus oryzae* (Quaas et al (1988) Eur. J. Biochem. 173:617) or Barnase from *Bacillus amyloliquefaciens* (Hartley (1988) J.Mol.Biol. 202:913).

So that the pollen-lethality DNA is expressed selectively in microspores or pollen of the maintainer plant, it is preferred that the pollen-specific promoter, which controls the pollen-lethality DNA in the pollen-lethality gene, be a promoter capable of directing gene expression selectively in the microspores and/or pollen of the plant. Such a pollen-specific promoter can be an endogeneous promoter or a foreign promoter and can be from the nuclear genome or from the mitochondrial or chloroplast genome of a plant cell, but in any event, the pollen-specific promoter is foreign in the nuclear genome of the plant being transformed. Preferably the pollen-specific promoter causes the pollen-lethality DNA to be expressed only in the microspores and/or pollen, i.e., after meiosis of the microsporocytes in the anthers. The pollen-specific promoter can be selected and isolated in a well known manner from a plant species, preferably the plant species to be rendered male-sterile, so that the pollen-specific promoter directs expression of the pollen-lethality DNA selectively in the microspores and/or pollen so as to kill or disable the microspores and/or pollen in which the pollen-lethality gene is expressed. The pollen-specific promoter is preferably also selected and isolated so that it is effective in preventing expressing of the pollen-lethality DNA in other tissues of the plant. For example, a suitable endogeneous pollen-specific promoter can be identified and isolated in a plant, to be rendered male-sterile, by:

1. searching for an mRNA which is only present in the plant during the development of its microspores and/or pollen;
2. optionally isolating the microspore- and/or pollen-specific mRNA;
3. preparing and isolating a cDNA from the microspore- and/or pollen-specific mRNA;
4. using this cDNA as a probe to identify regions in the plant genome which contain DNA coding for the corresponding microspore- and/or pollen-specific DNA or alternatively using inverse polymerase chain reactions for the geometric amplification of the DNA sequences which flank, upstream and downstream, a chosen core region of the genomic DNA corresponding to the sequence of the microspore- and/or pollen-specific cDNA; and
5. identifying the portion of the plant genome that is upstream (i.e., 5') from the DNA coding for the microspore- and/or pollen-specific mRNA and that contains the promoter of this DNA.

Examples of such pollen-specific promoters are well known (see MacCormick (1991) TIG 7:298). In this regard, Hamilton et al (1989) Sex. Plant Reprod. 2:208 describes a pollen-specific clone ("Zmg13") from maize inbred line W-22, and the use of the promoter sequences of the clone to direct pollen-specific expression in tobacco has been described by Guerrero et al (1990) Mol.Gen.Genet. 224:161). Other pollen-specific promoters that are likewise believed to be useful are the promoter of the gene corresponding to the *Nicotiana tabacum* pollen-specific cDNA NTPc303 described by Weterings et al (1992) Plant Mol. Biol. 18:1101; and the promoter of the gene corresponding to the *Brassica napus* pollen-specific cDNA B54 described by Shen and Hsu (1992) Mol. Gen. Genet. 234:379.

If the fertility-restorer DNA in the fertility-restorer gene of the maintainer gene is also expressed in microspores and/or pollen at the same time as the pollen-lethality DNA is expressed (due, for instance, to the activity of the restorer promoter in microspores and/or pollen), it is preferred that the pollen-lethality DNA be different from the male-sterility DNA (the expression of which is intended to be prevented by expression of the fertility-restorer DNA of the maintainer gene). For example, if the male-sterility DNA encodes Barnase in the male-sterile plants to be maintained, the fertility-restorer DNA in the maintainer gene should encode Barstar. Thus, if the restorer promoter in the maintainer gene also directs expression of the fertility-restorer DNA in microspores and/or pollen and at the same time as the pollen-lethality DNA is expressed, the pollen-lethality DNA preferably should not encode Barnase but rather, for example, another RNAse such as RNAse T1.

First and second marker DNAs and first and second marker promoters that can be used in the first and second marker genes of this invention are also well known (EP 0,344,029; EP 0,412,911). In this regard, it is preferred that the first and second marker DNAs be different, although the first and second marker promoters may be the same.

The fertility-restorer gene, the male-sterility gene, the pollen-lethality gene, and the first and second marker genes in accordance with this invention are generally foreign DNA sequences, preferably foreign chimaeric DNA sequences. Such foreign DNA sequences are preferably provided with suitable 3' transcription regulation sequences and polyadenylation signals, downstream (i.e., 3') from their respective fertility-restorer DNA, male-sterility DNA, pollen-lethality DNA, and first and second marker DNAs. In this regard, either foreign or endogenous, transcription termination and polyadenylation signals suitable for obtaining expression of such DNA sequences can be used. For example, the foreign 3' untranslated ends of genes, such as gene 7 (Velten and Schell (1985) Nucl. Acids Res. 13:6998), the octopine synthase gene (De Greve et al (1982) J.Mol. Appl. Genet. 1:499; Gielen et al (1983) EMBO J. 3:835; and Ingelbrecht et al (1989) The Plant Cell 1:671) the nopaline synthase gene of the T-DNA region of *Agrobacterium tumefaciens* Ti-plasmid (De Picker et al (1982) J.Mol. Appl. Genet. 1:561), the chalcone synthase gene (Sommer and Saedler (1986) Mol. Gen. Genet. 202: 429–434), and the CaMV 19S/39S transcription unit (Mogen et al (1990) The Plant Cell 2:1261–1272), can be used.

By "foreign" with regard to a gene or genotype of this invention is meant that the gene or genotype contains a foreign DNA sequence such as a male-sterility DNA, a fertility-restorer DNA, a pollen-lethality DNA, or a marker DNA and/or a foreign Promoter such as a sterility promoter, a restorer Promoter, a pollen-specific promoter or a marker Promoter. By "foreign" with regard to any DNA sequence, such as a coding sequence or a promoter, in a gene or genotype of this invention is meant that such a DNA is not in the same genomic environment in a plant cell, transformed with such a DNA in accordance with this invention, as is such a DNA when it is naturally found in the cell of the plant, bacteria, animal, fungus, virus or the like, from which such a DNA originates. This means, for example, that a foreign fertility-restorer DNA, male-sterility DNA, pollen-lethality DNA, or marker DNA can be: 1) a nuclear DNA in a plant of origin; 2) endogenous to the transformed plant cell (i.e., from a plant of origin with the same genotype as the plant being transformed); and 3) within the same transcriptional unit as its own endogenous promoter and 3' end transcription regulation signals (from the plant of origin) in the foreign gene or genotype in the transformed plant cell; but 4) inserted in a different place in the nuclear genome of the transformed plant cell than it was in the plant of origin so that it is not surrounded in the transformed plant cell by the genes which surrounded it naturally in the plant of origin. Likewise, a foreign fertility-restorer DNA, male-sterility DNA, pollen-lethality DNA, or marker DNA can also, for example, be: 1) a nuclear DNA in a plant of origin; and 2) endogenous to the transformed plant cell; but 3) in the same transcriptional unit as a different (i.e., not its own) endogenous promoter and/or 3' end transcription regulation signals in a foreign chimaeric gene or genotype of this invention in a transformed plant cell. A foreign fertility-restorer DNA, male-sterility DNA, pollen-lethality DNA, or marker DNA can also, for example, be: 1) a nuclear DNA in a plant of origin; and 2) endogenous to the transformed plant cell; but 3) in the same transcriptional unit as a heterologous promoter and/or 3' end transcription regulation signals in a foreign chimaeric gene or genotype of this invention in a transformed plant cell. A foreign fertility-restorer DNA, a male-sterility DNA, pollen-lethality DNA, or marker DNA can also, for example, be heterologous to the transformed plant cell and in the same transcriptional unit as an endogenous promoter and/or 3' transcription regulation signals (e.g., from the nuclear genome of a plant with the same genotype as the plant being transformed) in a foreign chimaeric DNA sequence of this invention in a transformed plant cell. Preferably, each fertility-restorer DNA, male-sterility DNA, pollen-lethality DNA, and marker DNA of this invention is heterologous to the plant cell being transformed.

BY "heterologous" with regard to a DNA, such as a fertility-restorer DNA, a male-sterility DNA, a pollen-lethality DNA, a marker DNA, a fertility-restorer promoter, a sterility promoter, a pollen-specific promoter or a marker promoter or any other DNA sequence in a gene or a genotype of this invention is meant that such a DNA is not naturally found in the nuclear genome of cells of a plant with the same genotype as the plant being transformed. Examples of heterologous DNAs include chloroplast and mitochondrial DNAs obtained from a plant with the same genotype as the plant being transformed, but preferred examples are chloroplast, mitochondrial, and nuclear DNAs from plants having a different genotype than the plant being transformed. DNAs from animal and bacterial genomes, and chromosomal and plasmidial DNAs from fungal, bacterial and viral genomes.

By "chimaeric" with regard to a foreign DNA sequence of this invention is meant that at least one of its coding sequences : 1) is not naturally found under the control of the promoter present in the foreign DNA sequence; and/or 2) is not naturally found in the same genetic locus as at least one of its associated marker DNAs. Examples of foreign chimaeric DNA sequences of this invention comprise a pollen-lethality DNA of bacterial origin under the control of a pollen-specific promoter of plant origin; and a pollen-lethality DNA of plant origin under the control of a pollen-specific promoter of plant origin and in the same genetic locus as a marker DNA of bacterial origin.

By "endogenous" with respect to a gene or genotype of this invention is meant that it is not foreign.

The foreign genes and genotypes of this invention, such as the male-sterility gene and genotype, the fertility-restorer gene and the pollen-lethality gene, can be describe like any other genotype: capital letters denote the presence of the foreign genes and genotypes (the dominant allele) while small letters denote their absence (the recessive allele). Hence, in this description of the invention, "S" and "s" will denote the respective presence and absence of the male-sterility gene, "R" and "r" will denote the respective presence and absence of the fertility-restorer gene, and "p" and "p" will denote the respective presence and absence of the maintainer gene.

For an endogeneous male-sterility genotype of this invention, "m" will denote the recessive allele, and "M" will denote the dominant allele. Thus, the recessive allele m in homozygous condition (m/m) at a male-sterility locus would result in male-sterility, and the dominant allele M, when present at a male-sterility locus either in homozygous or heterozygous condition, results in male-fertility.

The cell of a plant, particularly a plant capable of being infected with Agrobacterium such as most dicotyledonous plants (e.g., *Brassica napus*), can be transformed using a vector that is a disarmed Ti-plasmid containing the male-sterility gene and/or the fertility-restorer gene and/or the pollen-lethality gene and/or the maintainer gene and/or the marker gene(s) of this invention and carried by Agrobacterium. This transformation can be carried out using the procedures described, for example, in EP 0,116,718 and EP 0,270,822. Preferred Ti-plasmid vectors contain a foreign DNA sequence of this invention between the border sequences, or at least located to the left of the right border sequence, of the T-DNA of the Ti-plasmid. Of course, other types of vectors can be used to transform the plant cell, using procedures such as direct gene transfer (as described, for example, in EP 0, 233,247), pollen mediated transformation (as described, for example, in EP 0,270,356, PCT publication WO 85/01856, and U.S. Pat. No. 4,684,611), plant RNA virus-mediated transformation (as described, for example, in EP 0,067,553 and U.S. Pat. No. 4,407,956) and liposome-mediated transformation (as described, for example, in U.S. Pat. No. 4,536,475). Cells of monocotyledonous plants, such as the major cereals including corn, rice, wheat, barley and rye, can be transformed as described in PCT application PCT/EP 91/02198. In case the plant to be transformed is corn, other recently developed methods can also be used such as, for example, the methods described for certain lines of corn by Fromm et al (1990) Bio/Technology 8:833, Gordon-Kamm et al (1990) Bio/Technology 2:603 and Gould et al (1991) Plant Physiol. 95:426. In case the plant to be transformed is rice, recently developed methods can also be used such as, for example, the method described for certain lines of rice by Shimamoto et al (1989) Nature 338:274; Datta et al (1990) Bio/Technology 8:736; and Hayashimoto et al (1990) Plant Physiol. 93:857.

The so-transformed cell can be regenerated into a mature plant, and the resulting transformed plant can be used in a conventional breeding scheme to produce more transformed plants with the same characteristics or to introduce the male-sterility gene, the fertility-restorer gene, the pollen-lethality gene, the marker genes and/or the maintainer gene of this invention in other varieties of the same or related plant species. Seeds obtained from such plants contain the gene(s) of this invention as a stable genomic insert.

The maintainer plant of this invention is of the same species as a male-sterile plant line and can be used for the maintenance of the male-sterile line, i.e., to maintain a homogeneous population of male-sterile plants and a stock of pure seed of the female parent. The maintainer plant of this invention is itself a plant in which male-fertility has been restored and the genome of which contains both a male-sterility genotype and, in the maintainer locus, a fertility-restorer gene of this invention.

If a plant line with a homozygous male-sterility genotype ($A^{m/m}$ or $A^{S/S}$) is available, a maintainer plant for the male-sterile line can be directly obtained by transforming a male-sterile plant of the line with the maintainer gene of this invention and then selecting those transgenic plants which are male-fertility restored plants and in which the maintainer gene is stably integrated in the nuclear genome so that the genetic locus of the male-sterility genotype and of the maintainer gene are unlinked and segregate independently.

If the male-sterility genotype is foreign to the plant line, alternative strategies can be followed. For example, the maintainer plant of the present invention can be obtained by transforming a plant cell of the plant line (A) with the maintainer gene of this invention (P); and then regenerating, from the so-transformed plant cell, a transgenic plant containing, stably integrated in its genome, the maintainer gene. Such a transgenic plant ($A^{P/p}$) can then be crossed as a female parent with a plant $A^{S/s.R/r}$ of the same line, which contains at separate loci in its genome a male-sterility gene (S) and a corresponding fertility-restorer gene (R), both in heterozygous condition, but which lacks the maintainer gene. Thus, the cross is in fact: $A^{S/s.R/r.p/p}$ (male) x $A^{s/s.r/r.P/p}$ (female), and the offspring with the genotype $A^{S/s.r/r.P/p}$ (or hereinafter "$A^{S/s.P/p}$" for convenience) are selected and selfed. One eighth of the offspring that have the desired genotype ($A^{S/S.P/p}$) for a maintainer plant of this invention can then be selected. Another eighth of the offspring with the genotype ($A^{S/S,P/p}$) can be used as male-sterile plants to be maintained.

Isolation of plants with desired genotypes can be achieved by means of conventional testcrosses (see, e.g., Fehr (1987) supra), preferably supplemented by detection of the presence of specific genes at the DNA level, e.g., by means of amplification of DNA fragments by the polymerase chain reaction, by Southern blot analysis and/or by phenotypic analysis for the presence and expression of first or second marker genes of this invention.

The cross of a male-sterile plant containing a male-sterility genotype in homozygous condition ($A^{S/S}$ or $A^{m/m}$) with a maintainer plant of this invention ($A^{S/S,P/p}$ or $A^{m/m,P/p}$, respectively) results in a population of seeds that all contain the male-sterility genotype in homozygous condition ($A^{S/S}$ or $A^{m/m}$, respectively) because the maintainer gene is not transmitted through the pollen. This property can be used to advantage in maintaining the basic seed and in the multiplication of basic seed for the final production of parent seed.

The maintainer plants of this invention ($A^{S/S,P/p}$ or $A^{m/m,P/p}$) can themselves be maintained by selfing. The offspring of such selfing will consist of 50% male-fertile maintainer plants ($A^{S/S,P/p}$ or $A^{m/m,P/p}$, respectively) and 50% male-sterile plants containing the male-sterility genotype in homozygous condition ($A^{S/S}$ or $A^{m/m}$, respectively ). If desired, the male-sterile plants can be removed either manually on the basis of the male-sterile phenotype or, if the maintainer gene comprises a suitable first marker gene, preferably a first marker gene whose expression confers herbicide resistance to the plant, by using the phenotypic expression of the first marker gene (e.g. by applying herbicide to the offspring so that male-sterile plants that lack the herbicide-resistance gene are killed while maintainer plants with the herbicide-resistance gene survive).

Thus, the maintainer plant of this invention can be easily used to maintain a homogeneous population of male-sterile plants. In this regard, basic seed of a female parent of a given plant species can be crossed with an appropriate male parent to produce hybrid seed. Also, the maintainer plant of this invention can be used economically to multiply the basic seed of a female parent of a given plant species, so as to obtain sufficient quantities of female parent seed that can be crossed with an appropriate male parent to produce desired quantities of hybrid seed.

A male-sterile line, that is maintained and multiplied by the use of the maintainer plants of this invention, can be used for the production of hybrid seed. In principle, the male-sterile line ($A^{S/S}$) can be crossed directly with another male parent line ($B^{s/s}$) to produce hybrid seed ($AB^{S/s}$). However, since all hybrid plants are male-sterile, no reproduction and no seed set will occur. This is not a problem if the seed is not the harvested product (e.g., with lettuce), but where seed is the harvested product (e.g., with corn and oilseed rape), male-fertility in the hybrid plants should be at least partially restored. This can be accomplished by crossing the male-sterile line with a male-fertile parent line (e.g., $B^{R/R}$) that is also a restorer line, i.e. that also contains a fertility-restorer gene (R). The hybrids produced ($AB^{S/s,R/r}$) will be fully male-fertile. Alternatively the male-sterile-line ($A^{s/s}$) can first be crossed with the male-fertile line ($A^{s/s}$) just prior to hybrid seed production. This has the advantage of giving a further multiplication of the female parent line. The offspring ($A^{S/s}$) can then be crossed with a suitable male-fertile parent line ($B^{s/s,r/r}$) to produce hybrid seed that is 50% male-fertile. If hybrid seed with 100% male fertility is desired, the offspring can be crossed with a suitable restorer male parent line ($B^{s/s,R/R}$).

In the case of a male-sterile line in which male-sterility is due to an endogenous male-sterility genotype ($A^{m/m}$) at a male-sterility locus, hybrid seed can easily be produced by crossing the male-sterile line ($A^{m/m}$) with a line that is homozygous with respect to the endogenous dominant (male-fertility) allele at that male-sterility locus ($B^{M/M}$). All hybrid offspring of this cross will have the genotype $AB^{M/m}$ and will be fertile.

The maintainer plants of this invention can also be used as pollinator (i.e., male-fertile) plants in a cross with wild-type plants ($A^{s/s,P/p}$) of the same inbred line. The progeny of this cross will all be male-sterile and heterozygous for the male-sterility genotype ($A^{S/s,P/p}$). The progeny can therefore be used directly for hybrid seed production by crossing with a pollinator plant line B ($B^{s/s,p/p}$). This scheme only requires a male-sterilization of the wild-type plants, for example by manually removing the anthers (e.g., in corn) or by using a male gametocide.

Of course, by using the maintainer plants of this invention to maintain a homogeneous population of plants that are homozygous with respect to a male-sterility allele (whether dominant or recessive) that is encoded in the nuclear genome, the maintainer plants acquire many of the characteristics of plants of a cytoplasmic male-sterile line. However, such plants do not have one of the major disadvantages of cytoplasmic male-sterile plants, namely the cytoplasmic uniformity of the various male-sterile lines which, in corn, has led to serious problems (see Craig (1977) In "Corn and Corn Improvement", G. F. Sprague, ed., American Society of Agronomy, Inc., Publisher, p. 671).

Thus, the maintainer gene of this invention, when introduced into a particular line of a plant species, can always be introduced into any other line by backcrossing, but since the maintainer gene can only be transmitted through an egg, it will always be associated with the cytoplasm of the line in which it was initially introduced. However, since a maintainer plant line is only used for maintenance of a male-sterile line and not as a female parent for hybrid seed production, the hybrid seed will always contain the cytoplasm of the female parent, as desired.

The following Examples illustrate this invention. Unless otherwise indicated, all experimental procedures for manipulating recombinant DNA were carried out by the standardized procedures described in Sambrook et al (1989) "Molecular Cloning: A Laboratory Manual, Second Edition", Cold Spring Harbor Laboratory Press, N.Y. USA. All polymerase chain reactions ("PCR") were performed under conventional conditions, using the Vent™ polymerase (Cat. No. 254L—Biolabs New England, Beverley, Mass. 01915, U.S.A.) isolated from *Thermococcus litoralis* (Neuner et al (1990) Arch. Microbiol. 153:205–207). Oligonucleotides were designed by the methods described by Kramer and Fritz (1968) Methods in Enzymology 154:350 and synthesized by the phosphoramidite method (Beaucage and Caruthers (1981) Tetrahedron Letters 22:1859) on an applied Biosystems 380A DNA synthesizer (Applied Biosystems B.V., Maarssen, Netherlands).

The following bacterial strains and plasmids, used in the Examples, are available from the Deutsche Sammlung für Mikroorganismen und Zellkulturen ("DSM"), Mascheroder Weg 1B, Braunschweig, Germany:

| Bacterial strain | plasmid | DSM No | Date of Deposit |
|---|---|---|---|
| E. coli WK6 | pMa5-8 | DSM 4567 | May 3, 1988 |
| E. coli WK6 | pMc5-8 | DSM 4566 | May 3, 1988 |

In the Examples, reference will be made to the following Figure and Sequence Listing:

| Sequence Listing | |
|---|---|
| SEQ ID no. 1: | genomic DNA comprising the promoter of the Zm13 gene from Zea mays |
| SEQ ID no. 2: | sequence of plasmid "pVE144" |
| SEQ ID no. 3: | sequence of plasmid "pVE108" |
| SEQ ID no. 4: | sequence of oligonucleotide "MDB80" |
| SEQ ID no. 5: | sequence of oligonucleotide "MDB81" |
| SEQ ID no. 6: | sequence of oligonucleotide "MDB82" |
| SEQ ID No. 7: | genomic DNA comprising the anther specific promoter "PT72" from rice |
| SEQ ID No. 8: | genomic DNA comprising the anther specific promoter "PT42" from rice |
| SEQ ID No. 9: | genomic DNA comprising the anther specific promoter "PE1" from rice |
| SEQ ID No. 10: | genomic DNA comprising the anther specific promoter "PCA55" from corn |
| SEQ ID No. 11: | Oligonucleotide Zm13OLI2 |
| SEQ ID No. 12: | Oligonucleotide Zm13OLI1 |
| SEQ ID No. 13: | Oligonucleotide Zm13OLI5 |
| SEQ ID No. 14: | Oligonucleotide BXOL2 |
| SEQ ID No. 15: | Oligonucleotide TA29SBXOL2 |
| SEQ ID No. 16: | Oligonucleotide PTA29OL5 |
| SEQ ID No. 17: | EcoRI-HindIII fragment of pTS218 carrying the maintainer gene. |

EXAMPLES

Example 1

Isolation of the pollen-specific promoter of the Zm13 gene from maize

A pollen-specific cDNA from Zea mays inbred line W-22, designated as "Zmc13", has been isolated and characterized by Hanson et al (1989) The Plant Cell 1:173. The corresponding genomic clone, designated as "Zmg13", containing substantial portions of the 5' flanking region has been isolated and characterized by Hamilton et al (1989) Sex. Plant Reprod. 2:208 (see also Hamilton et al (1992) Plant Mol. Biol. 18:211). The complete sequence of Zmg13 is shown in SEQ ID no. 1, and its promoter region will hereinafter be referred to as the "Zm13 promoter".

A corresponding promoter region from corn inbred line H99 was isolated as follows. Genomic DNA of inbred line H99 was prepared as described by Dellaporta et al (1983) Plant Mol. Biol. Reports 1:19–21. Using the genome as a substrate, a 1471 bp fragment was amplified by PCR using the oligonucleotides MDB80 and MDB82, the sequences of which are shown in SEQ ID no. 4 and SEQ ID no. 6, respectively. MDB80 corresponds to nucleotides 8 to 28 of Zmg13, while MDB82 is complementary to nucleotides 1458 to 1478 of Zmg13. Then, the purified amplified 1471 bp fragment was used as a substrate for the amplification by PCR of a 1422 bp fragment, using the oligonucleotides MDB80 and MDB81. MDB81 is complementary to nucleotides 1409 to 1429 of Zmg13, and its sequence is shown in SEQ ID no. 5. By using MDB81, a NcoI site is created in the amplified 1422 bp fragment at the ATG translation initiation codon.

The 1422 bp fragment is then ligated in an SmaI site of pGEM2 (Promega Corporation, Madison, Wisconsin 53711, U.S.A.), yielding plasmid pMDB13, and the fragment is sequenced (Maxam and Gilbert (1980) Meth. Enzymol. 65:499). The pollen-specific promoter of the Zm13 gene of corn inbred line H99 is obtained from pMDB13 as a EcoRV-NcoI fragment.

The Zm13 promoter is also cloned as follows. Genomic DNA of Zea mays line H99 is prepared as described above. Using the genomic DNA as a substrate, the following two fragments are amplified by means of PCR: 1) a 875 bp fragment is amplified using the oligonucleotides MDB80 (SEQ ID No. 4) and ZM13OLI2 (which is complementary to nucleotides 859 to 882 of Zmg13 and which sequence is given in SEQ ID No. 11); and 2) a 661 bp fragment is amplified using the oligonucleotides Zm13OLI1 (which corresponds to nucleotides 767 to 791 of Zmg13 and which sequence is given in SEQ ID No. 12) and Zm13OLI5 (which is partially complementary to nucleotides 1397 to 1423 of Zmg13 and which sequence is given in SEQ ID No. 13). The 875 bp fragment, corresponding to the upstream region of the Zm13 promoter, is cloned into the SmaI site of pGEM2, yielding plasmid pTS204. The 661 bp fragment, corresponding to the downstream region of the Zm13 promoter, is digested with NcoI and cloned into plasmid pJB66 (Botterman and Zabeau (1987) DNA 6:583) digested with EcoRV and NcoI, yielding plasmid pTS203. Both fragments partly overlap and share a BstXI site in the region of overlap. Ligation of the 567 bp EcoRV-BstXI fragment of pTS204 and the 638 bp BstXI-NcoI fragment of pTS203 results in a 1205 bp fragment corresponding to the Zm13 promoter. This 1205 bp fragment, as cloned from line H99, is sequenced, and its sequence is found to be identical to the corresponding fragment of Zmg13 from line W-22 as given in SEQ ID No.1 except at position 276 (G in W-22 is T in H99), 410 (G in) W-22 is A in H99), and 1205–1206 (GC in W-22 is GGC in H99, thus corresponding to a 1 nucleotide insertion), numberings being as in SEQ ID No. 1.

Example 2

Construction of plant transformation vectors comprising a maintainer gene that contain DNA encoding Barstar under the control of the TA29 promoter and DNA encoding Barnase under the control of the Zm13 promoter The 1205 bp EcoRV-NcoI fragment of pMDB13 is ligated to the large EcoRI-SmaI fragment of plasmid pVE144 and to the 739 bp EcoRI-NcoI fragment of pVE108, yielding plasmid pGSJVR1. Plasmid pVE144, the sequence of which is shown in SEQ ID no. 2, is a plasmid derived from plasmid pUC18 (Yanisch-Perron et al (1985) Gene 33:103) and containing DNA, encoding neomycin phosphotranferase (neo) under the control of the 35S3 promoter (EP 0.359.617) from Cauliflower Mosaic Virus isolate CabbB-JI (Hull and Howell (1978) Virology 86:482) and DNA encoding the Barstar (Hartley (1988) J.Mol.Biol. 202:913) under the control of the tapetum-specific promoter of the TA29 gene of Nicotiana tabacum (EP 0.344.029; Seurinck et al (1990) Nucleic Acids Res. 18:3403). Plasmid pVE108, the sequence of which is shown in SEQ ID no. 3, is a plasmid derived from pUC18 and containing DNA encoding phosphinothricin acetyl transferase (bar) (EP 0.242.236) under the control of the 35S3 promoter and DNA encoding Barnase (Hartley (1980) supra) under the control of the TA29 promoter. The resulting plasmid, pGSJVR1 (which is subsequently renamed "pTS210"), is a pUC18-derived plasmid that contains a maintainer gene of this invention comprising: DNA encoding Barnase as the pollen-lethality DNA, the Zm13 promoter as the pollen-specific promoter, DNA encoding Barstar as the fertility-restorer DNA, the TA29 promoter as the restorer promoter, neo as the first marker DNA and the 35S3 promoter as the first marker promoter.

pTS210 is also obtained as follows. The 0.9 kb BstXI-SacI fragment of pTS204 is ligated to the large BstXI-SacI fragment of pTS203, yielding plasmid pTS206. The 1.47 BglII-NcoI kb fragment of pTS206 is then ligated to the large NcoI-BglII fragment of pVE108, yielding plasmid pTS207. Finally, the 1.9 kb EcoRV-Eco-RI fragment of pTS207 is ligated to the large Eco-RI-SmaI fragment of pVE144, yielding plasmid pTS210.

A plasmid pTS218, which differs from pTS210 by carrying the bar gene as a selectable marker gene, is also obtained as follows:

- a 255 bp DNA fragment, designated as bxx and carrying the translation initiation site of the PTA29-barstar gene, is obtained by PCR using pVE144 as a template and oligonucleotides BXOL2 (SEQ ID No. 14) and TA29SBXOL2 (SEQ ID No. 15) as primers.

- a 492 bp DNA fragment is prepared by PCR using pVE108 and bxx as a template and oligonucleotides PTA29OL5 (SEQ ID No. 16) and BXOL2 as primers. This 492 bp fragment is digested with AsnI and BspEI, and a 274 bp fragment is purified on gel and ligated to the 6.28 kb fragment of pVE144 which was digested with BspEI and partially digested with AsnI. The resulting plasmid is designated as pVE144 and carries the PTA29-barstar-3'nos chimeric gene with an optimized translational initiation context.

- pVEK144 is digested with MunI and HindIII, and the 3.7 kbp fragment is isolated and ligated to the 1.7 kbp MunI-HindIII fragment of pVE108, yielding plasmid pVEB144 which carries the PTA29-barstar-3'nos and the P35S-bar-3'nos chimeric genes.

- the EcoRI-HindIII fragment of pVEB144, containing the two chimeric genes, is ligated to the large EcoRI-HindIII fragment of pUCNew2, yielding plasmid pVEC144. pUCNew2 is derived from pUC19 as described in WO 92/13956.

- finally, the large EcoRI-SmaI fragment of pVEC144 is ligated to the 1.9 bp EcoRV-EcoRI fragment of pTS207, yielding plasmid pTS218.

Plasmid pTS182 carries three chimeric genes, i.e., PTA29-barstar-3'nos (with optimized translational initiation context), P35S-bar-3'nos, and PZM13-barnase-3'nos. The EcoRI-HindIII fragment of pTS18 2carrying these three chimeric genes is presented in the sequence listing as SEQ ID No. 17.

All steps of vector construction involving fragments of the barnase DNA, such as pVE108, pVE144, and pTS102, are carried out in *E. coli* strain MC1061 containing the cointegrate plasmid R702::pMc5BS which is obtained as follows. Plasmid pMc5BS, containing the barstar gene (encoding an inhibitor of barnase) under the control of the tac promoter (De Boer et al (1983) Proc. Natl. Acad. Sci. USA 80:21), is constructed by: cloning the EcoRI-HindIII fragment of plasmid pMT416 (Hartley (1988) supra) into the EcoRI and HindIII sites of plasmid pMc5-8 (DSM 4566); and then deleting the sequence starting with the initiation codon of the phoA signal sequence and ending with the last nucleotide before the translation initiation codon of the barstar-coding region by means of a looping-out mutagenesis procedure as generally described by Sollazo et al (1985) Gene 37:199.

Plasmid R702 is from *Proteus mirabilis* and can replicate in *E. coli* (Villarroel et al (1983) Mol. Gen. Genet. 189:390). Plasmid R702::pMc5BS is obtained by cointegration through illegitimate recombination between pMc5BS and R702, mediated by transposable elements present on R702 (Leemans (1982) "Technieken voor het gebruik van Ti-plasmieden van *Agrobacterium tumefaciens* als vectoren voor de genetic engineering van planten", Ph.D. Thesis Vrije Universiteit Brussel, Brussels, Belgium) and checked for induced expression of Barstar.

The use of *E. coli* (R702::pMc5BS) allows the construction, maintenance, amplification, and purification of plasmids containing the barnase DNA, such as pGSJVR1, without any lethal effect on the host due to accidental expression of the barnase DNA. However, because the Zm13 promoter is not expressed in *E. coli*, all steps of vector construction involving this promoter are also carried out in *E. coli* strain MC1061.

Example 3

Transformation of corn with the maintainer gene of Example 2

Zygotic immature embryos of about 0.5 to 1 mm are isolated from developing seeds of corn inbred line H99. The freshly isolated embryos are enzymatically treated for 1–2 minutes with an enzyme solution II (0.3% macerozyme (Kinki Yakult, Nishinomiya, Japan) in CPW salts (Powell & Chapman (1985) "Plant cell Culture, A Practical Approach", R. A. Dixon ed., Chapter 3) with 10% mannitol and 5 mM 2-[N-Morpholino] ethane sulfonic acid (MES), pH 5.6). After 1–2 minutes incubation in this enzyme solution, the embryos are carefully washed with N6aph solution (macro- and micro-elements of N6 medium (Chu et al (1975) Sci. Sin. Peking 18:659) supplemented with 6 mM asparagine, 12 mM proline, 1 mg/l thiamine-HCl, 0.5 mg/l nicotinic acid, 100 mg/l casein hydrolysate, 100 mg/l inositol, 30 g/l sucrose and 54 g/l mannitol). After washing, the embryos are incubated in the maize electroporation buffer, EPM-KCl (80 mM KCl, 5 mM $CaCl_2$, 10 mM HEPES (N-2-hydroxyethylpiperazine-N'-2-ethanesulfonic acid) and 0.425M mannitol, pH 7.2). Approximately 100 embryos in 200 µl EPM-KCl are loaded in each electroporation cuvette. About 20 µg of a plasmid DNA, pPGSJVR1 (of Example 2) linearized with EcoRI, is added per cuvette.

After 1 hour DNA incubation with the explants, the cuvettes are transferred to an ice bath. After 10 minutes incubation on ice, the electroporation is carried out: one pulse with a field strength of 375 V/cm is discharged from a 900 µF capacitor. The electroporation apparatus is as described by Dekeyser et al (1990) The Plant Cell 2:591. Immediately after electroporation, fresh liquid N6aph substrate is added to the explants in the cuvette, after which the explants are incubated for a further 10 minute period on ice.

Afterwards, the embryos are transferred to Mahl VII substrate (macro- and micro-elements and vitamins of N6 medium supplemented with 100 mg/l casein hydrolysate, 6 mM proline, 0.5 g/l MES, 1 mg/l 2,4-dichlorophenoxyacetic acid (2,4-D) and 2% sucrose solidified with 0.75 g/l $MgCl_2$ and 1.6 g/l Phytagel (Sigma Chemical Company, St Louis, Mo. U.S.A.), pH 5.8) and supplemented with 0.2M mannitol. After 3 days, the embryos are transferred to the same substrate supplemented with 200 mg/l kanamycin. After approximately 14 days, the embryos are transferred to Mahl VII substrate without mannitol, supplemented with kanamycin. The embryos are further subcultured on this selective substrate for approximately 2 months with subculturing intervals of about 3 weeks. The induced embryogenic tissue is carefully isolated and transferred to MS medium (Murashige and Skoog (1962) Physiol. Plant 15:473) supplemented with 5 mg/l 6-benzylaminopurine for line H99. The embryogenic tissue is maintained on this medium for approximately 14 days and subsequently transferred to MS medium without hormones and 6% sucrose for line H99.

Developing shoots are transferred to ½ MS medium with 1.5% sucrose for further development to normal plantlets. These plantlets are transferred to soil and cultivated in the greenhouse.

In an analogous way, corn embryos are transformed with a fragment of pTS218 DNA which contains the maintainer gene and the chimeric P35S-bar-3'nos and which is obtained by digestion of the plasmid with EcoRI, XhoI and PstI and by purifying the longest fragment. Transformation and plant regeneration is as described in Example 5.

Example 4

Analysis of the transgenic corn plants of Example 3

Plants form Example 3 transformed with pGSJVR1 are analysed for the presence of the maintainer gene by means of PCR. DNA is prepared according to the protocol described by Dellaporta et al (1983) Plant Mol. Biol. Reporter 1:19, adapted for application to tissue amounts of about 10 to 20 mg. For each plant, such an amount of tissue is macerated in extraction buffer in a microfuge tube. Representative fragments of the maintainer gene are amplified using appropriate oligonucleotide probes.

Activity of the expression product of the first marker gene (i.e., neomycin phosphotransferase II (NPTII)) is assayed in plants as follows. Crude extracts are prepared by grinding plant tissue in extraction buffer (McDonnell et al (1987) Plant Molecular Biol. Reporter 5:380). The extracts are then subjected to non-denaturing polyacrylamide gel electrophoresis according to the procedure described by Reiss et al (1984) Gene 30:211. NPTII activity is then assayed by in situ phosphorylation of kanamycin using [gamma-32P]ATP as a substrate (McDonnell et al (1987) supra).

The plants that are found to be positive on both the PCR and NPTII assays are further analyzed by means of Southern hybridization. Genomic DNA is prepared from plant tissue according to the protocol described by Dellaporta et al (1983) supra, supplemented by a treatment with RNase to remove remaining RNA. A non-transformed H99 plant is used as a control. Samples of the DNA are digested with appropriate restriction enzymes and subjected to horizontal agarose electrophoresis. Southern transfer to Hybond N+ (Amersham International PLC, Amersham, United Kingdom) membranes by means of the "alkali blotting of DNA" protocol and the subsequent hybridization are performed as recommended by the manufacturer (Amersham Hybond-N+ leaflet). Suitable radioactive probes are prepared with the multi-prime DNA labelling kit (Amersham) according to the protocol supplied by the manufacturer which is derived from published procedures (Feinberg and Vogelstein (1983) Anal. Biochem. 132:6). The banding patterns show that at least the maintainer gene is integrated into the plant genomic DNA.

The PCR assays show that the maintainer gene is present. The NPTII assays show that the first marker DNA is expressed. The mature transformed plants can then be analyzed phenotypically to see whether the barstar DNA is expressed in tapetum cells and the barnase gene is expressed in pollen cells. Expression of barstar is determined by northern blotting of anther mRNA and by making testcrosses to determine the restoration in the progeny. Expression of the Pollen-lethality gene is determined by cytological examination of the anther. In this regard, viable and nonviable mature pollen is determined by analyzing the staining of isolated pollen upon incubation for 30 minutes at 24° C. in the following reaction mixture: 100 mm phosphate buffer pH 7.8, 100 mm Sodiumsuccinate and 1 mM NitroBlue Tetrazolium, followed by visual inspection of formazan precipitation in viable pollen. Alternative techniques for the differentiation between viable and nonviable mature pollen are those described, for example, by Alexander (1969) Stain Technology 44:117, and by Heslop-Harrison and Heslop-Harrison (1970) Stain Technology 45:115. The viability of microspores is determined by embedding flower buds in plastic at different developmental stages and subjecting the buds to histochemical staining with the succinate dehydrogenase assay, both as described by De Block and Debrouwer (1992) The Plant Journal 2:261.

Ultimately, the progeny of the plant transformed with the pollen-lethality gene is determined. None of the offspring obtained from a cross using this plant as a male parent have this gene, while 50% of the offspring obtained from a cross using this plant as a female parent possess the gene.

Plants from Example 3, transformed with pTS218 DNA, are analyzed in the same way, except that the expression product of the first marker gene, i.e., phosphinothricine acetyltransferase, is assayed by means of a PAT assay as described in Example 5.

Example 5

Production of male-sterile corn plants

Zygotic embryos of corn inbred line H99 were isolated, enzymatically treated, washed, and loaded in electroporation buffer as described in Example 3. Approximately 100 embryos in 200 µl EPM-KCl were loaded in each electroporation cuvette. About 20 µg of a plasmid DNA, pVE108 linearized with HindIII, was added per cuvette. pVE108 is a 5620 bp plasmid which contains: a chimaeric gene comprising the bar DNA (EP 242236), encoding phosphinothricin acetyl transferase (PAT) and conferring resistance to an herbicidal glutamine synthetase inhibitor such as phosphinothricin (PPT), under the control of the 35S3 promoter; and another chimaeric gene comprising the DNA coding for barnase (Hartley (1988) supra) under the control of the tapetum-specific promoter of the TA29 gene (EP 344029) of *N. tabacum*. The complete sequence of plasmid pVE108 is given in SEQ ID no. 4. All vector constructions involving DNA fragments comprising the barnase gene were carried out in *E. coli* strain MC1061 containing the plasmid R702::pMc5BS of Example 3. After a 1 hour DNA incubation with the explants, the cuvettes were transferred to an ice bath. After 10 minutes incubation on ice, the electroporation was carried out as described in Example 3. Immediately after electroporation, fresh liquid N6aph substrate was added to the explants in the cuvette, after which the explants were incubated for a further 10 minute period on ice.

Afterwards, the embryos from one electroporation experiment were transferred to Mahl VII substrate supplemented with 0.2M mannitol and 2 mg/l PPT. After approximately 14 days, the embryos were transferred to Mh1 VII substrate (Mahl VII substrate of Example 3 but without proline and casein hydrolysate) supplemented with 2 mg/l PPT but without mannitol. After approximately 4 weeks, the embryos were subcultured for another month on Mh1 VII substrate supplemented with 10 mg/l PPT. The induced embryogenic tissue was carefully isolated and transferred to MS medium supplemented with 5 mg/l 6-benzylaminopurine. The embryogenic tissue was maintained on this medium for approximately 14 days, and subsequently transferred to MS medium without hormones and sucrose. Developing shoots were transferred to ½ MS medium with 1.5% sucrose for further development to normal plantlets. These plantlets survived an in vitro spraying with doses of BASTA® (Hoechst AG, Frankfurt an Main, Germany) corresponding to 2 l/ha. These plantlets were then transferred to soil and cultivated in the greenhouse, and two of the transformed plantlets, designated RZM35-1 and RZM35-18, were further characterized.

The embryos from a second electroporation experiment were transferred to Mh1 VII substrate supplemented with 2 mg/l PPT and 0.2M mannitol. After about 14 days, the embryos were transferred to Mh1 VII substrate supplemented with 2 mg/l PPT but without mannitol. After approximately another three weeks, the embryos were transferred to Mh1 VII substrate supplemented with 10 mg/l PPT but without mannitol. After another three weeks, the induced embryogenic tissue was carefully isolated and transferred to MS medium supplemented with 2 mag/l PPT and 5 mg/l 6-benzylaminopurine. The embryogenic tissue was maintained on this medium for approximately 14 days and subsequently transferred to MS medium without hormones, sucrose or PPT. Developing shoots were transferred to ½ MS medium with 1.5% sucrose for further development to normal plantlets. The resulting plantlets were transferred to soil and cultivated in the greenhouse, and three of the transformed plantlets, designated RZM34-1, RZM34-12, and RZM34-14, were further characterized.

RZM34-1, RZM34-12, RZM34-14, RZM35-1, and RZM35-18 were grown in the greenhouse. Activity of the expression product of the bar gene in leaves of the plants was assayed as follows in a "PAT assay". 100 mg of leaf tissue from each plant, together with 50 mg of acid-treated sea sand (Merck, Darmstadt, Germany) and 5 mg polyvinylpolypyrrolidone (PVPP), were ground in an Eppendorf tube with a glass rod in 50 µl of extraction buffer (25 mM Tris-HCL pH 7.5, 1 mM $Na_2$-EDTA (ethylenediaminetetraacetic acid disodium salt), 0.15 mg/ml phenylmethylsulfonylfluoride (PMSF), 0.3 mg/ml dithiothreitol (DTT), and 0.3 mg/ml bovine serum albumin). The extract was centrifuged in a microfuge for 5 minutes at 16000 rpm. The supernatant was recovered and diluted ten times with TE 25/1 (25 mM Tris-HCL pH 7.5, 1 mM $Na_2$-EDTA. To twelve µl of the diluted extract was then added: 1 µl of 1 mM PPT in TE 25/1, 1 µl of 2 mM AcetylCoenzyme A in TE 25/1, and 2 µl of [14C] AcetylCoenzym A (60 mCi/mmol, 0.02 mCi/ml, [NEN Research Products, Dupont, Wilmington, Del., USA). The reaction mixture was incubated for 30 minutes at 37° C. and spotted on a aluminium sheet silica gel 60 t.l.c. plate with concentrating zone (Merck). Ascending chromatography was carried out in a 3 to 2 mixture of 1-propanol and $NH_4OH$ (25% $NH_3$). C14 was visualized by overnight autoradiography (XAR-5 Kodak film). The tolerance to the herbicide BASTA® was tested by brushing a small area near the top of one leaf per plant with a 1% solution of the herbicide and observing the damage symptoms at and near the brushed sites. While RZM34-1, RZM35-1 and RZM35-18 showed no damage symptoms at all, RZM34-12 and RZM34-14 displayed slight browning and drying-out of the brushed site. RZM34-1, RZM34-12, RZM34-14, RZM35-1 and RZM35-18 were also shown to be male-sterile but otherwise phenotypically completely normal; female fertility, for instance, was normal. The spikelets of the male flowers were of about normal length but were very thin and appeared to be empty, and they never opened. A detailed analysis showed that the anthers were reduced to almost microscopic structures. This phenotype indicates not only that at least one copy of the barnase gene was expressed, but also that it was selectively expressed in some or all of the tissues of the anthers.

Southern analysis showed RZM35-1 and RZM35-18 to have an identical integration pattern, with only one copy of plasmid pVE108 being present in the genome of each plant. A small part of the plasmid DNA sequence adjacent to the HindIII site (used for linearization prior to electroporation) seemed to be absent in the integrated copy. Southern analysis of RZM34-1, RZM34-12 and RZM34-14 showed that each of these plants probably has two or three copies of part or all of pVE108 integrated into its genome. The copies are most likely not inserted in a concatemer configuration.

Transformants RZM35-1 and RZM34-1 were pollinated with pollen from an untransformed H99 plant, and progeny plantlets were recovered. From the 35 plantlets recovered from RZM35-1, 16 (46%) scored positive in a PAT assay, while 19 (54%) were PAT negative. This proportion in the F1 progeny does not differ significantly from the 1:1 ratio expected under normal Mendelian segregation of one active copy of the chimaeric bar gene (X2=0.26).

From the 34 plantlets recovered from RZM34-1, 19 (56%) scored positive in a PAT assay, while 15 (44%) were PAT negative. This proportion in the F1 progeny does not differ significantly from the 1:1 ratio expected under normal Mendelian segregation, assuming that the transformed female parent had one active copy, or alternatively multiple active, but closely linked copies, of the chimaeric bar gene (X2=0.47).

Example 6
Production of restorer corn plants

Zygotic, embryos of corn inbred line H99 were isolated, enzymatically treated, washed and loaded in electroporation buffer as described in Example 5. Approximately 100 embryos in 200 µl EPM-KCl were loaded in each electroporation cuvette. About 20 µg of a plasmid DNA, pVE144 linearized with HindIII, was added per cuvette. pVE144 is a 6555 bp plasmid which was described in Example 2.

The embryos were electroporated, and the transformed cells were selected, grown into callus, and regenerated as described in Example 3. Transgenic plants were analyzed for the presence of the fertility-restorer gene and the marker gene by means of Southern hybridization and PCR. The expression of the fertility-restorer gene is assayed by means of Northern blotting, and the expression of the marker gene is determined by NPTII assay as described in Example 3.

Example 7
Production of maintainer corn plants and a male-sterile corn line and maintenance of the male-sterile corn line Maintainer plants of this invention of corn line H99 are obtained as outlined in FIG. 1. A plant of corn inbred line H99 with the male-sterility genotype $H99^{s/s,r/r,p/p}$, transformed with the male-sterility gene of Example 5, is crossed with plants with the genotype $H99^{s/s,R/r,p/p-}$, transformed with the fertility-restorer gene of Example 6. The progeny that have the genotype $H99^{S,s/R/r,p/p}$ are identified by PCR analysis for the presence of the S and R genes. These plants are selfed, yielding progeny with nine different genotypes. Two of these genotypes ($H99_{S/S,r/r}$ and $H99_{S/s,r/r}$) will develop into male-sterile plants, while all the other genotypes will develop into male-fertile plants. When these male-fertile plants are selfed, progeny analysis allows the identification of their genotype. Thus: a) the progeny of selfings of $H99^{S/S,R/R}$, $H99^{S/s,R/R}$, $H99^{s/s,R/R}$, $H99^{s/s,R/r}$ and $H99^{s/s,r/r}$ would all develop into male-fertile plants; b). selfings of $H99^{S/s,R/r}$ plants would produce progeny, of which 13 out of 16 would be male-fertile, and since the male-sterility gene is linked to the herbicide resistance gene, bar, 4 out of the 13 male-fertile plants would be sensitive to the herbicide BASTA$^R$; and c) selfings of $H99_{S/S,R/r}$ plants would produce progeny, of which 12 out 16 would be fertile (4 out of 16 would have the genotype $H99^{S/S,R/R}$ and 8 out of 16 would have the genotype $H99^{S/S,R/r}$) all of which would be resistant to the herbicide, and the male-sterile progeny of which (4 out of 16) would all be homozygous for the male-sterility gene ($H99_{S/S,r/r}$).

The homozygous male-sterile progeny ($H99^{S/S,r/r}$) of selfing (c) are then crossed with their male-fertile siblings, and only when the cross is with plants with the genotype $H99^{S/S,R/r}$ are the resulting plants 50% male-sterile (all with the genotype $H99^{S/S,r/r}$) and 50% male-fertile (all with the genotype $H99^{S/S,R/r}$. Indeed, the alternative cross between $H99^{S/S,r/r}$ and $H99^{S/S,R/R}$ would result in 100% male-fertile progeny plants.

Maintainer plants are selected by crossing the plant with the genotype $H99^{S/s,R/r,p/p}$ with a plant that is heterozygous for the maintainer gene of Example 2, i.e., ($H99^{s/s,r/r,P/p}$), using the latter plant as the female parent. The offspring with the genotype $H99^{S/s,r/r,P/p}$ are selected by means of testcrosses supplemented with PCR analysis of the progeny (which can be easily identified by PCR and Southern blotting for the presence of the S and P genes and the absence of the R gene). The selected fertile offspring are then selfed. One out of eight offspring have the desired genotype for a maintainer plant of this invention ($H99^{S/S,P/p}$) and can be further selected by means of testcrosses and PCR analysis of the progeny. Indeed, only plants with this genotype will produce 50% male-sterile offspring (all $H99^{S/S,p/p}$) and 50% male-fertile offspring (all $H99^{S/S,P/p}$), thus growing at once both the desired homozygous male-sterile line and the maintainer line of this invention. Testcrosses also include the pollination of wild type H99 plants with pollen of the progeny plants obtained from the selfing of $H99^{S/s,P/p}$ plants.

Homozygous male-sterile plants with the genotype $H99^{S/S,r/r,P/p}$ are then pollinated by maintainer plants ($H99^{S/S,r/r,P/p}$) of this invention. All progeny have the genotype $H99^{S/S,r/r,p/p}$, so that the male-sterile line is maintained, as desired.

Example 8

Introduction of the male-sterility gene and the maintainer gene in inbred corn lines through classical breeding The male-sterility gene of Example 5 and the maintainer gene of Example 2 are transferred from corn inbred line H99 to another corn inbred line (A) by repeated backcrossings as follows. The maintainer plant $H99^{S/S,P/p}$ is crossed as a female parent with an untransformed plant of line A ($A^{s/s,p/p}$). The offspring with the genotype $A-H99^{S/s,P/p}$ are selected by screening, using PCR, for the presence of both the maintainer gene (P) and the male-sterility gene (S). These plants are then crossed again as female parents with $A^{s/s,p/p}$ plants, and the offspring that are heterozygous for both the P and S genes are again selected by PCR. This process of backcrossing is repeated until finally plants with the genotype $A^{S/s,P/p}$ are obtained. These plants are then selfed, and the progeny are analyzed in the same way as described in Example 7. In this way, male-sterile plants with the genotype $A^{S/S,p/p}$ and maintainer plants of this invention with the genotype $A^{S/S,P/p}$ are obtained.

SEQUENCE LISTING ( 1 ) GENERAL INFORMATION:

( i i i ) NUMBER OF SEQUENCES: 17

( 2 ) INFORMATION FOR SEQ ID NO: 1:

( i ) SEQUENCE CHARACTERISTICS:
    ( A ) LENGTH: 2661 base pairs
    ( B ) TYPE: nucleic acid
    ( C ) STRANDEDNESS: double
    ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
    ( A ) ORGANISM: Zea mays
    ( B ) STRAIN: inbred line W-22

( x ) PUBLICATION INFORMATION:
    ( A ) AUTHORS: Hamilton et al.,
    ( C ) JOURNAL: Sex Plant Reprod.
    ( D ) VOLUME: 2
    ( F ) PAGES: 208-
    ( G ) DATE: 1989

( x i ) SEQUENCE DESCRIPTION: SEQ ID NO: 1:

```
AAAGACCCCG  CTTGTCAGTG  AATGTTGCTA  TTCTAGCAAA  GGGAAGGTAT  TTTTCGGAC       60

CTTCGGCGTA  AAGCCTTCGT  CCAGATCGCA  ATCTAAATTT  ATTATTTTGA  ACAAATTAAT     120

ATTGCGAGGG  GCTACTGTTG  GGGACCTTCG  GCATCCGAAG  GTCCTCAAAA  ACAGGATTTA     180

ATAGTGTTTC  TGGAGTATAA  TGTGTGAACA  GATATCTTCG  GACTCAAGTC  AGGCATCACA     240

GTAGACCAGA  ATAATACGAA  GGTTGGTGAA  GCGCCGAAGG  TGTAAGCAGG  AAAGCTTCGG     300
```

-continued

```
CAAGACAGCA GCAGTTGAAA CCGACTTAAA GATGAAAAGG CTATTTAGAC CTCAACAGAT   360
TACTATAGGT TTATTATTAA GTGTAAAGGG CATTAATGTA ATTTTGCACG GGCTACGTCC   420
CGTGCCTATA AATAGGTGAA CAGTATTCCC GTACTGTTCA CGCTGACTTG GCATTCGCTT   480
TTTGCGTCAC GCTTGTACTG TCATCTCATT CCTATTGAAG GTACACTTGT AATTCAACGA   540
TATTTCTGTT TGTACCTAAT AATAATATAT AATTGTTCAT GTTGTCTTTT ATATTCTTTA   600
TATTTCATCC TTCGTCATTG TTAATGAAT TTATGAAGGT ACGTCCTTCA TAACCTTCGT   660
CCGTAAACCA TTATATCCTA AGGGAAATAA TGCTTCGAAG GACGAAGGAC CTTAACGATT   720
AATATTTTCT ATGTTGCCTT GTTCTTAACT CATAGCACTT GAGAACAAGT CTCCAACAGT   780
TTGGTTATTC CTATTCCACG TGGATTAGAT GAGATTTAGA TAAAATTAGA AATAATTTTG   840
ACTTACTAGG GATTTAAACC AACTCAGTCC CGTTCAATCC ACATGGATTG AGATTAAAAC   900
AACTATTGAG ATTTATTGT ATCAACACTC AACACCGATG TGTTTTTATA ATACATCTTG   960
CGTGACATTT GTCCAAGTAC TATGCTAAAT ATGAGAAGCT GCCATTTAGT GATTCTATAT  1020
ACTATTCACT TATGGATACA TTAACTGAT ACCGTTTTGT TGAGCGCGTC TTATTTAGTT  1080
TTACATAGCA GCATAGAAGA TTAGAAGTCG CAAATCCAAC TTTTGTGGAC CGCTGAAAAA  1140
CTCAACCAAA TTCGACATAT TTTTCACCTC CCCATGCCAC AAAACTAGGT CAAAACGGCT  1200
TTCTGCCGTC GGCCACTATT TCTACGGGCA GCCAGACAAA TCTTCGGGTC TCGCAGATTA  1260
TTTAAGGACA CCACAGGCTG CGTTACGAAA CCAGGCCAGA TTTGCCACCC TCGTCTCACC  1320
CTCCCTCCCT CACACAAATA ATAAGGAAAG GTCCCGCCCT TTTCCTCCGA CATCCACAAG  1380
GGGGGAGGGG AAAACACGTA CATTCACCCG GCGGCAATAA TGGCCTCGGT TCCGGCTCCG  1440
GCGACGACGA CCGCCGCCGT CATCCTATGC CTATGCGTCG TCCTCTCCTG TGCCGCGGCT  1500
GACGACCCGA ACCTCCCCGA CTACGTCATC CAGGGCCGCG TGTACTGCGA CACCTGCCGC  1560
GCCGGGTTCG TGACCAACGT CACCGAGTAC ATCGCGGGCG CCAAGGTGAG GCTGGAGTGC  1620
AAGCACTTCG GCACCGGCAA GCTCGAGCGC GCCATCGACG GGTCACCGA CGCGACCGGC  1680
ACCTACACGA TCGAGCTCAA GGACAGCCAC GAGGAGGACA TCTGCCAGGT GGTGCTGGTG  1740
GCCAGCCCGC GCAAGGACTG CGACGAGGTC CAGGCGCTCA GGGACCGCGC CGGCGTCCTG  1800
CTCACCAGGA ACGTTGGCAT CTCCGACAGC CTGCGCCCCG CCAACCCGCT AGGCTACTTC  1860
AAGGACGTGC CGCTCCCCGT CTGCGCCGCG CTGCTCAAGC AGCTGGACTC GGACGACGAC  1920
GACGACCAGT AAACTATACC ACGGCGGCGT CGCGGACATG CTGCACAAAA CTACAACGAT  1980
ACAGAGCGAA CGCATGGCAT GGATAGCAGT ATCTACGGAA AGAAAGGAA GAAAGGAAA  2040
ATAAAAAATG TATCAGAGTG CTTGATTCAC TTGCTGCTGT CACCCATTCC CCGTTCTTAA  2100
CATAACATGT GGGCCGGCTT GGCCCAGGCA CAAGCCCATC TACGCATGGC CTACGGTCCG  2160
CTAAAATATA GCCCTAATTA TGAGCCGTGT TGTGCCGTCA CATGGATCGA TCCAGCGGCA  2220
TACGATACAA CCCACAATTA CTTATGTGTG ATGGGCCGGC CAAAAAGCC TAAGATGTCG  2280
TAGTGTGCTA GACCGACTCA TATATATAAA ACATTAAAAC ATATTGTCGG GGACCATAAT  2340
TAGGGGTACC CTTAAGGCTC CTAATTCTCA GCTGGTAACC CTCATCAGCG TAAAGCTGCA  2400
AAGGCCTGAT GGGTGCGATT AAGTCAGGGA TCAGTCCATT CGAGGGACTC GATCACGCCT  2460
CGCCCGAGCC TAGCCTCGGA CAAGGGCAGC CGACCCCGGA GGATCTCCGT CTCGCCCGAG  2520
GCCCTCCTCC AGCGGCGAAC ATATTTCCGG CTCGCCCGAG GCCCTGTCTT CGCCAAGAAG  2580
CAACCCTGAC CAAATCGCCG CACCGACCGA CCAAATCGCA GGAGCATTTA ATGCAAAGGT  2640
GGCCTGACAC ATTTATCCTG A                                           2661
```

( 2 ) INFORMATION FOR SEQ ID NO: 2:

( i ) SEQUENCE CHARACTERISTICS:
        ( A ) LENGTH: 6555 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: plasmid pVE144 (replicable in E.coli)

( i x ) FEATURE:
        ( A ) NAME/KEY: -
        ( B ) LOCATION: 1..396
        ( D ) OTHER INFORMATION: /label=pUC18
            / note= "pUC18 derived sequence"

( i x ) FEATURE:
        ( A ) NAME/KEY: -
        ( B ) LOCATION: complement (397..751)
        ( D ) OTHER INFORMATION: /label=3'nos
            / note= "3'regulatory sequence containing the
            polyadenylation site derived from Agrobacterium
            T-DNA nopaline synthase gene"

( i x ) FEATURE:
        ( A ) NAME/KEY: -
        ( B ) LOCATION: complement (752..1024)
        ( D ) OTHER INFORMATION: /label=barstar
            / note= "coding region of the barstar gene of
            Bacillus amyloliquefaciens"

( i x ) FEATURE:
        ( A ) NAME/KEY: -
        ( B ) LOCATION: complement (1025..1607)
        ( D ) OTHER INFORMATION: /label=TA29
            / note= "promoter derived from the TA29 gene of
            Nicotiana tabacum"

( i x ) FEATURE:
        ( A ) NAME/KEY: -
        ( B ) LOCATION: 1608..2440
        ( D ) OTHER INFORMATION: /label=35S3
            / note= "35S3 promoter sequence derived from
            cauliflower mosaic virus isolate CabbB-JI"

( i x ) FEATURE:
        ( A ) NAME/KEY: -
        ( B ) LOCATION: 2441..3256
        ( D ) OTHER INFORMATION: /label=neo
            / note= "coding region of the neomycine
            phosphotransferase gene of Tn5"

( i x ) FEATURE:
        ( A ) NAME/KEY: -
        ( B ) LOCATION: 3257..4315
        ( D ) OTHER INFORMATION: /label=3'ocs
            / note= "3'regulatory sequence containing the
            polyadenylation site derived from Agrobacterium
            T-DNA octopine synthase gene"

( i x ) FEATURE:
        ( A ) NAME/KEY: -
        ( B ) LOCATION: 4316..6555
        ( D ) OTHER INFORMATION: /label=pUC18
            / note= "pUC18 derived sequence"

( x i ) SEQUENCE DESCRIPTION: SEQ ID NO: 2:

```
TCGCGCGTTT    CGGTGATGAC    GGTGAAAACC    TCTGACACAT    GCAGCTCCCG    GAGACGGTCA         60

CAGCTTGTCT    GTAAGCGGAT    GCCGGGAGCA    GACAAGCCCG    TCAGGGCGCG    TCAGCGGGTG        120
```

```
TTGGCGGGTG TCGGGGCTGG CTTAACTATG CGGCATCAGA GCAGATTGTA CTGAGAGTGC    180
ACCATATGCG GTGTGAAATA CCGCACAGAT GCGTAAGGAG AAAATACCGC ATCAGGCGCC    240
ATTCGCCATT CAGGCTGCGC AACTGTTGGG AAGGGCGATC GGTGCGGGCC TCTTCGCTAT    300
TACGCCAGCT GGCGAAAGGG GGATGTGCTG CAAGGCGATT AAGTTGGGTA ACGCCAGGGT    360
TTTCCCAGTC ACGACGTTGT AAAACGACGG CCAGTGAATT CGAGCTCGGT ACCCGGGGAT    420
CTTCCCGATC TAGTAACATA GATGACACCG CGCGCGATAA TTTATCCTAG TTTGCGCGCT    480
ATATTTGTT TTCTATCGCG TATTAAATGT ATAATTGCGG GACTCTAATC ATAAAACCC      540
ATCTCATAAA TAACGTCATG CATTACATGT TAATTATTAC ATGCTTAACG TAATTCAACA    600
GAAATTATAT GATAATCATC GCAAGACCGG CAACAGGATT CAATCTTAAG AAACTTTATT    660
GCCAAATGTT TGAACGATCT GCTTCGGATC CTCTAGACCA AGCTAGCTTG CGGGTTTGTG    720
TTTCCATATT GTTCATCTCC CATTGATCGT ATTAAGAAAG TATGATGGTG ATGTCGCAGC    780
CTTCCGCTTT CGCTTCACGG AAAACCTGAA GCACACTCTC GGCGCCATTT TCAGTCAGCT    840
GCTTGCTTTG TTCAAACTGC CTCCATTCCA AAACGAGCGG GTACTCCACC CATCCGGTCA    900
GACAATCCCA TAAAGCGTCC AGGTTTTCAC CGTAGTATTC CGGAAGGGCA AGCTCCTTTT    960
TCAATGTCTG GTGGAGGTCG CTGATACTTC TGATTTGTTC CCCGTTAATG ACTGCTTTTT   1020
TCATCGGTAG CTAATTTCTT TAAGTAAAAA CTTTGATTTG AGTGATGATG TTGTACTGTT   1080
ACACTTGCAC CACAAGGGCA TATATAGAGC ACAAGACATA CACAACAACT TGCAAAACTA   1140
ACTTTTGTTG GAGCATTTCG AGGAAAATGG GGAGTAGCAG GCTAATCTGA GGGTAACATT   1200
AAGGTTTCAT GTATTAATTT GTTGCAAACA TGGACTTAGT GTGAGGAAAA AGTACCAAAA   1260
TTTTGTCTCA CCCTGATTTC AGTTATGGAA ATTACATTAT GAAGCTGTGC TAGAGAAGAT   1320
GTTTATTCTA GTCCAGCCAC CCACCTTATG CAAGTCTGCT TTTAGCTTGA TTCAAAAACT   1380
GATTTAATTT ACATTGCTAA ATGTGCATAC TTCGAGCCTA TGTCGCTTTA ATTCGAGTAG   1440
GATGTATATA TTAGTACATA AAAAATCATG TTTGAATCAT CTTTCATAAA GTGACAAGTC   1500
AATTGTCCCT TCTTGTTTGG CACTATATTC AATCTGTTAA TGCAAATTAT CCAGTTATAC   1560
TTAGCTAGAT GGGGATCCTC TAGAGTCGAC CTGCAGGCAT GCAAGCTCCT ACGCAGCAGG   1620
TCTCATCAAG ACGATCTACC CGAGTAACAA TCTCCAGGAG ATCAAATACC TTCCCAAGAA   1680
GGTTAAAGAT GCAGTCAAAA GATTCAGGAC TAATTGCATC AAGAACACAG AGAAAGACAT   1740
ATTTCTCAAG ATCAGAAGTA CTATTCCAGT ATGGACGATT CAAGGCTTGC TTCATAAACC   1800
AAGGCAAGTA ATAGAGATTG GAGTCTCTAA AAAGGTAGTT CCTACTGAAT CTAAGGCCAT   1860
GCATGGAGTC TAAGATTCAA ATCGAGGATC TAACAGAACT CGCCGTGAAG ACTGGCGAAC   1920
AGTTCATACA GAGTCTTTTA CGACTCAATG ACAAGAAGAA AATCTTCGTC AACATGGTGG   1980
AGCACGACAC TCTGGTCTAC TCCAAAAATG TCAAAGATAC AGTCTCAGAA GACCAAAGGG   2040
CTATTGAGAC TTTTCAACAA AGGATAATTT CGGGAAACCT CCTCGGATTC CATTGCCCAG   2100
CTATCTGTCA CTTCATCGAA AGGACAGTAG AAAAGGAAGG TGGCTCCTAC AAATGCCATC   2160
ATTGCGATAA AGGAAAGGCT ATCATTCAAG ATGCCTCTGC CGACAGTGGT CCCAAAGATG   2220
GACCCCCACC CACGAGGAGC ATCGTGGAAA AAGAAGACGT TCCAACCACG TCTTCAAAGC   2280
AAGTGGATTG ATGTGACATC TCCACTGACG TAAGGGATGA CGCACAATCC CACTATCCTT   2340
CGCAAGACCC TTCCTCTATA TAAGGAAGTT CATTTCATTT GGAGAGGACA CGCTGAAATC   2400
ACCAGTCTCT CTCTATAAAT CTATCTCTCT CTCTATAACC ATGGATCCGG CCAAGCTAGC   2460
TTGGATTGAA CAAGATGGAT TGCACGCAGG TTCTCCGGCC GCTTGGGTGG AGAGGCTATT   2520
```

| | | | | | |
|---|---|---|---|---|---|
| CGGCTATGAC | TGGGCACAAC | AGACAATCGG | CTGCTCTGAT | GCCGCCGTGT | TCCGGCTGTC | 2580 |
| AGCGCAGGGG | CGCCCGGTTC | TTTTTGTCAA | GACCGACCTG | TCCGGTGCCC | TGAATGAACT | 2640 |
| GCAGGACGAG | GCAGCGCGGC | TATCGTGGCT | GGCCACGACG | GGCGTTCCTT | GCGCAGCTGT | 2700 |
| GCTCGACGTT | GTCACTGAAG | CGGGAAGGGA | CTGGCTGCTA | TTGGGCGAAG | TGCCGGGGCA | 2760 |
| GGATCTCCTG | TCATCTCACC | TTGCTCCTGC | CGAGAAAGTA | TCCATCATGG | CTGATGCAAT | 2820 |
| GCGGCGGCTG | CATACGCTTG | ATCCGGCTAC | CTGCCCATTC | GACCACCAAG | CGAAACATCG | 2880 |
| CATCGAGCGA | GCACGTACTC | GGATGGAAGC | CGGTCTTGTC | GATCAGGATG | ATCTGGACGA | 2940 |
| AGAGCATCAG | GGGCTCGCGC | CAGCCGAACT | GTTCGCCAGG | CTCAAGGCGC | GCATGCCCGA | 3000 |
| CGGCGAGGAT | CTCGTCGTGA | CCCATGGCGA | TGCCTGCTTG | CCGAATATCA | TGGTGGAAAA | 3060 |
| TGGCCGCTTT | TCTGGATTCA | TCGACTGTGG | CCGGCTGGGT | GTGGCGGACC | GCTATCAGGA | 3120 |
| CATAGCGTTG | GCTACCCGTG | ATATTGCTGA | AGAGCTTGGC | GGCGAATGGG | CTGACCGCTT | 3180 |
| CCTCGTGCTT | TACGGTATCG | CCGCTCCCGA | TTCGCAGCGC | ATCGCCTTCT | ATCGCCTTCT | 3240 |
| TGACGAGTTC | TTCTGAGCGG | GACTCTGGGG | TTCGAAATGA | CCGACCAAGC | GACGCCCAAC | 3300 |
| CTGCCATCAC | GAGATTTCGA | TTCCACCGCC | GCCTTCTATG | AAAGGTTGGG | CTTCGGAATC | 3360 |
| GTTTTCCGGG | ACGCCGGCTG | GATGATCCTC | CAGCGCGGGG | ATCTCATGCT | GGAGTTCTTC | 3420 |
| GCCCACCCCC | TGCTTTAATG | AGATATGCGA | GACGCCTATG | ATCGCATGAT | ATTTGCTTTC | 3480 |
| AATTCTGTTG | TGCACGTTGT | AAAAAACCTG | AGCATGTGTA | GCTCAGATCC | TTACCGCCGG | 3540 |
| TTTCGGTTCA | TTCTAATGAA | TATATCACCC | GTTACTATCG | TATTTTTATG | AATAATATTC | 3600 |
| TCCGTTCAAT | TTACTGATTG | TACCCTACTA | CTTATATGTA | CAATATTAAA | ATGAAAACAA | 3660 |
| TATATTGTGC | TGAATAGGTT | TATAGCGACA | TCTATGATAG | AGCGCCACAA | TAACAAACAA | 3720 |
| TTGCGTTTTA | TTATTACAAA | TCCAATTTTA | AAAAAGCGG | CAGAACCGGT | CAAACCTAAA | 3780 |
| AGACTGATTA | CATAAATCTT | ATTCAAATTT | CAAAAGGCCC | CAGGGGCTAG | TATCTACGAC | 3840 |
| ACACCGAGCG | GCGAACTAAT | AACGTTCACT | GAAGGGAACT | CCGGTTCCCC | GCCGGCGCGC | 3900 |
| ATGGGTGAGA | TTCCTTGAAG | TTGAGTATTG | GCCGTCCGCT | CTACCGAAAG | TTACGGGCAC | 3960 |
| CATTCAACCC | GGTCCAGCAC | GGCGGCCGGG | TAACCGACTT | GCTGCCCCGA | GAATTATGCA | 4020 |
| GCATTTTTTT | GGTGTATGTG | GGCCCCAAAT | GAAGTGCAGG | TCAAACCTTG | ACAGTGACGA | 4080 |
| CAAATCGTTG | GGCGGGTCCA | GGGCGAATTT | GCGACAACA | TGTCGAGGCT | CAGCAGGGGC | 4140 |
| TCGATCCCCT | CGCGAGTTGG | TTCAGCTGCT | GCCTGAGGCT | GGACGACCTC | GCGGAGTTCT | 4200 |
| ACCGGCAGTG | CAAATCCGTC | GGCATCCAGG | AAACCAGCAG | CGGCTATCCG | CGCATCCATG | 4260 |
| CCCCCGAACT | GCAGGAGTGG | GGAGGCACGA | TGGCCGCTTT | GGTCGACCTG | CAGCCAAGCT | 4320 |
| TGGCGTAATC | ATGGTCATAG | CTGTTTCCTG | TGTGAAATTG | TTATCCGCTC | ACAATTCCAC | 4380 |
| ACAACATACG | AGCCGGAAGC | ATAAAGTGTA | AAGCCTGGGG | TGCCTAATGA | GTGAGCTAAC | 4440 |
| TCACATTAAT | TGCGTTGCGC | TCACTGCCCG | CTTTCCAGTC | GGGAAACCTG | TCGTGCCAGC | 4500 |
| TGCATTAATG | AATCGGCCAA | CGCGCGGGGA | GAGGCGGTTT | GCGTATTGGG | CGCTCTTCCG | 4560 |
| CTTCCTCGCT | CACTGACTCG | CTGCGCTCGG | TCGTTCGGCT | GCGGCGAGCG | GTATCAGCTC | 4620 |
| ACTCAAAGGC | GGTAATACGG | TTATCCACAG | AATCAGGGGA | TAACGCAGGA | AAGAACATGT | 4680 |
| GAGCAAAAGG | CCAGCAAAAG | GCCAGGAACC | GTAAAAAGGC | CGCGTTGCTG | GCGTTTTTCC | 4740 |
| ATAGGCTCCG | CCCCCCTGAC | GAGCATCACA | AAAATCGACG | CTCAAGTCAG | AGGTGGCGAA | 4800 |
| ACCCGACAGG | ACTATAAAGA | TACCAGGCGT | TTCCCCCTGG | AAGCTCCCTC | GTGCGCTCTC | 4860 |
| CTGTTCCGAC | CCTGCCGCTT | ACCGGATACC | TGTCCGCCTT | TCTCCCTTCG | GGAAGCGTGG | 4920 |

-continued

| | | | | | |
|---|---|---|---|---|---|
| CGCTTTCTCA | ATGCTCACGC | TGTAGGTATC | TCAGTTCGGT | GTAGGTCGTT | CGCTCCAAGC | 4980
| TGGGCTGTGT | GCACGAACCC | CCCGTTCAGC | CCGACCGCTG | CGCCTTATCC | GGTAACTATC | 5040
| GTCTTGAGTC | CAACCCGGTA | AGACACGACT | TATCGCCACT | GGCAGCAGCC | ACTGGTAACA | 5100
| GGATTAGCAG | AGCGAGGTAT | GTAGGCGGTG | CTACAGAGTT | CTTGAAGTGG | TGGCCTAACT | 5160
| ACGGCTACAC | TAGAAGGACA | GTATTTGGTA | TCTGCGCTCT | GCTGAAGCCA | GTTACCTTCG | 5220
| GAAAAAGAGT | TGGTAGCTCT | TGATCCGGCA | AACAAACCAC | CGCTGGTAGC | GGTGGTTTTT | 5280
| TTGTTTGCAA | GCAGCAGATT | ACGCGCAGAA | AAAAGGATC | TCAAGAAGAT | CCTTTGATCT | 5340
| TTTCTACGGG | GTCTGACGCT | CAGTGGAACG | AAAACTCACG | TTAAGGGATT | TTGGTCATGA | 5400
| GATTATCAAA | AAGGATCTTC | ACCTAGATCC | TTTTAAATTA | AAAATGAAGT | TTTAAATCAA | 5460
| TCTAAAGTAT | ATATGAGTAA | ACTTGGTCTG | ACAGTTACCA | ATGCTTAATC | AGTGAGGCAC | 5520
| CTATCTCAGC | GATCTGTCTA | TTTCGTTCAT | CCATAGTTGC | CTGACTCCCC | GTCGTGTAGA | 5580
| TAACTACGAT | ACGGGAGGGC | TTACCATCTG | GCCCCAGTGC | TGCAATGATA | CCGCGAGACC | 5640
| CACGCTCACC | GGCTCCAGAT | TTATCAGCAA | TAAACCAGCC | AGCCGGAAGG | GCCGAGCGCA | 5700
| GAAGTGGTCC | TGCAACTTTA | TCCGCCTCCA | TCCAGTCTAT | TAATTGTTGC | CGGGAAGCTA | 5760
| GAGTAAGTAG | TTCGCCAGTT | AATAGTTTGC | GCAACGTTGT | TGCCATTGCT | ACAGGCATCG | 5820
| TGGTGTCACG | CTCGTCGTTT | GGTATGGCTT | CATTCAGCTC | CGGTTCCCAA | CGATCAAGGC | 5880
| GAGTTACATG | ATCCCCCATG | TTGTGCAAAA | AAGCGGTTAG | CTCCTTCGGT | CCTCCGATCG | 5940
| TTGTCAGAAG | TAAGTTGGCC | GCAGTGTTAT | CACTCATGGT | TATGGCAGCA | CTGCATAATT | 6000
| CTCTTACTGT | CATGCCATCC | GTAAGATGCT | TTTCTGTGAC | TGGTGAGTAC | TCAACCAAGT | 6060
| CATTCTGAGA | ATAGTGTATG | CGGCGACCGA | GTTGCTCTTG | CCCGGCGTCA | ATACGGGATA | 6120
| ATACCGCGCC | ACATAGCAGA | ACTTTAAAAG | TGCTCATCAT | TGGAAAACGT | TCTTCGGGGC | 6180
| GAAAACTCTC | AAGGATCTTA | CCGCTGTTGA | GATCCAGTTC | GATGTAACCC | ACTCGTGCAC | 6240
| CCAACTGATC | TTCAGCATCT | TTTACTTTCA | CCAGCGTTTC | TGGGTGAGCA | AAAACAGGAA | 6300
| GGCAAAATGC | CGCAAAAAAG | GGAATAAGGG | CGACACGGAA | ATGTTGAATA | CTCATACTCT | 6360
| TCCTTTTTCA | ATATTATTGA | AGCATTTATC | AGGGTTATTG | TCTCATGAGC | GGATACATAT | 6420
| TTGAATGTAT | TTAGAAAAAT | AAACAAATAG | GGGTTCCGCG | CACATTTCCC | CGAAAAGTGC | 6480
| CACCTGACGT | CTAAGAAACC | ATTATTATCA | TGACATTAAC | CTATAAAAAT | AGGCGTATCA | 6540
| CGAGGCCCTT | TCGTC | | | | | 6555

( 2 ) INFORMATION FOR SEQ ID NO: 3:

( i ) SEQUENCE CHARACTERISTICS:
        ( A ) LENGTH: 5620 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: plasmid pVE108 (replicable in E.coli)

( i x ) FEATURE:
        ( A ) NAME/KEY: -
        ( B ) LOCATION: 1..395
        ( D ) OTHER INFORMATION: /label=pUC18
            / note= "pUC18 derived sequence"

( i x ) FEATURE:
  ( A ) NAME/KEY: -
  ( B ) LOCATION: complement (396..802)
  ( D ) OTHER INFORMATION: /label=3'nos
    / note= "3'regulatory sequence containing the
    polyadenylation site derived from the nopaline
    synthase gene from Agrobacterium T-DNA"

( i x ) FEATURE:
  ( A ) NAME/KEY: -
  ( B ) LOCATION: complement (803..1138)
  ( D ) OTHER INFORMATION: /label=barnase
    / note= "coding region of the barnase gene of
    Bacillus amyloliquefaciens"

( i x ) FEATURE:
  ( A ) NAME/KEY: -
  ( B ) LOCATION: complement (1139..1683)
  ( D ) OTHER INFORMATION: /label=TA29
    / note= "sequence derived from tapetum specific
    promoter of Nicotiana tabacum"

( i x ) FEATURE:
  ( A ) NAME/KEY: -
  ( B ) LOCATION: 1684..2516
  ( D ) OTHER INFORMATION: /label=35S3
    / note= "'35S3'promoter sequence derived from
    cauliflower mosaic virus isolate CabbB-JI"

( i x ) FEATURE:
  ( A ) NAME/KEY: -
  ( B ) LOCATION: 2517..3068
  ( D ) OTHER INFORMATION: /label=bar
    / note= "coding sequence of phosphinotricin
    acetyltransferase gene"

( i x ) FEATURE:
  ( A ) NAME/KEY: -
  ( B ) LOCATION: 3069..3356
  ( D ) OTHER INFORMATION: /label=3'nos
    / note= "3'regulatory sequence containing the
    polyadenylation site derived from Agrobacterium
    T-DNA nopaline synthase gene"

( i x ) FEATURE:
  ( A ) NAME/KEY: -
  ( B ) LOCATION: 3357..5620
  ( D ) OTHER INFORMATION: /label=pUC18
    / note= "pUC18 derived sequence"

( x i ) SEQUENCE DESCRIPTION: SEQ ID NO: 3:

```
TCGCGCGTTT  CGGTGATGAC  GGTGAAAACC  TCTGACACAT  GCAGCTCCCG  GAGACGGTCA    60
CAGCTTGTCT  GTAAGCGGAT  GCCGGGAGCA  GACAAGCCCG  TCAGGGCGCG  TCAGCGGGTG   120
TTGGCGGGTG  TCGGGCTGG   CTTAACTATG  CGGCATCAGA  GCAGATTGTA  CTGAGAGTGC   180
ACCATATGCG  GTGTGAAATA  CCGCACAGAT  GCGTAAGGAG  AAAATACCGC  ATCAGGCGCC   240
ATTCGCCATT  CAGGCTGCGC  AACTGTTGGG  AAGGGCGATC  GGTGCGGGCC  TCTTCGCTAT   300
TACGCCAGCT  GGCGAAAGGG  GGATGTGCTG  CAAGGCGATT  AAGTTGGGTA  ACGCCAGGGT   360
TTTCCCAGTC  ACGACGTTGT  AAAACGACGG  CCAGTGAATT  CGAGCTCGGT  ACCCGGGGAT   420
CTTCCCGATC  TAGTAACATA  GATGACACCG  CGCGCGATAA  TTTATCCTAG  TTTGCGCGCT   480
ATATTTGTT   TTCTATCGCG  TATTAAATGT  ATAATTGCGG  GACTCTAATC  ATAAAACCC    540
ATCTCATAAA  TAACGTCATG  CATTACATGT  TAATTATTAC  ATGCTTAACG  TAATTCAACA   600
GAAATTATAT  GATAATCATC  GCAAGACCGG  CAACAGGATT  CAATCTTAAG  AAACTTTATT   660
GCCAAATGTT  TGAACGATCT  GCTTCGGATC  CTCTAGAGNN  NNCCGGAAAG  TGAAATTGAC   720
CGATCAGAGT  TTGAAGAAAA  ATTTATTACA  CACTTTATGT  AAAGCTGAAA  AAAACGGCCT   780
CCGCAGGAAG  CCGTTTTTTT  CGTTATCTGA  TTTTTGTAAA  GGTCTGATAA  TGGTCCGTTG   840
```

```
TTTTGTAAAT  CAGCCAGTCG  CTTGAGTAAA  GAATCCGGTC  TGAATTTCTG  AAGCCTGATG   900
TATAGTTAAT  ATCCGCTTCA  CGCCATGTTC  GTCCGCTTTT  GCCCGGGAGT  TTGCCTTCCC   960
TGTTTGAGAA  GATGTCTCCG  CCGATGCTTT  TCCCCGGAGC  GACGTCTGCA  AGGTTCCCTT  1020
TTGATGCCAC  CCAGCCGAGG  GCTTGTGCTT  CTGATTTTGT  AATGTAATTA  TCAGGTAGCT  1080
TATGATATGT  CTGAAGATAA  TCCGCAACCC  CGTCAAACGT  GTTGATAACC  GGTACCATGG  1140
TAGCTAATTT  CTTTAAGTAA  AAACTTTGAT  TTGAGTGATG  ATGTTGTACT  GTTACACTTG  1200
CACCACAAGG  GCATATATAG  AGCACAAGAC  ATACACAACA  ACTTGCAAAA  CTAACTTTTG  1260
TTGGAGCATT  TCGAGGAAAA  TGGGGAGTAG  CAGGCTAATC  TGAGGGTAAC  ATTAAGGTTT  1320
CATGTATTAA  TTTGTTGCAA  ACATGGACTT  AGTGTGAGGA  AAAAGTACCA  AAATTTTGTC  1380
TCACCCTGAT  TTCAGTTATG  GAAATTACAT  TATGAAGCTG  TGCTAGAGAA  GATGTTTATT  1440
CTAGTCCAGC  CACCCACCTT  ATGCAAGTCT  GCTTTTAGCT  TGATTCAAAA  ACTGATTTAA  1500
TTTACATTGC  TAAATGTGCA  TACTTCGAGC  CTATGTCGCT  TTAATTCGAG  TAGGATGTAT  1560
ATATTAGTAC  ATAAAAAATC  ATGTTTGAAT  CATCTTTCAT  AAAGTGACAA  GTCAATTGTC  1620
CCTTCTTGTT  TGGCACTATA  TTCAATCTGT  TAATGCAAAT  TATCCAGTTA  TACTTAGCTA  1680
GATCCTACGC  AGCAGGTCTC  ATCAAGACGA  TCTACCCGAG  TAACAATCTC  CAGGAGATCA  1740
AATACCTTCC  CAAGAAGGTT  AAAGATGCAG  TCAAAAGATT  CAGGACTAAT  TGCATCAAGA  1800
ACACAGAGAA  AGACATATTT  CTCAAGATCA  GAAGTACTAT  TCCAGTATGG  ACGATTCAAG  1860
GCTTGCTTCA  TAAACCAAGG  CAAGTAATAG  AGATTGGAGT  CTCTAAAAAG  GTAGTTCCTA  1920
CTGAATCTAA  GGCCATGCAT  GGAGTCTAAG  ATTCAAATCG  AGGATCTAAC  AGAACTCGCC  1980
GTGAAGACTG  GCGAACAGTT  CATACAGAGT  CTTTACGAC  TCAATGACAA  GAAGAAAATC  2040
TTCGTCAACA  TGGTGGAGCA  CGACACTCTG  GTCTACTCCA  AAAATGTCAA  AGATACAGTC  2100
TCAGAAGACC  AAAGGGCTAT  TGAGACTTTT  CAACAAAGGA  TAATTTCGGG  AAACCTCCTC  2160
GGATTCCATT  GCCCAGCTAT  CTGTCACTTC  ATCGAAAGGA  CAGTAGAAAA  GGAAGGTGGC  2220
TCCTACAAAT  GCCATCATTG  CGATAAAGGA  AAGGCTATCA  TTCAAGATGC  CTCTGCCGAC  2280
AGTGGTCCCA  AAGATGGACC  CCCACCCACG  AGGAGCATCG  TGGAAAAAGA  AGACGTTCCA  2340
ACCACGTCTT  CAAAGCAAGT  GGATTGATGT  GACATCTCCA  CTGACGTAAG  GGATGACGCA  2400
CAATCCCACT  ATCCTTCGCA  AGACCCTTCC  TCTATATAAG  GAAGTTCATT  TCATTTGGAG  2460
AGGACACGCT  GAAATCACCA  GTCTCTCTCT  ATAAATCTAT  CTCTCTCTCT  ATAACCATGG  2520
ACCCAGAACG  ACGCCCGGCC  GACATCCGCC  GTGCCACCGA  GGCGGACATG  CCGGCGGTCT  2580
GCACCATCGT  CAACCACTAC  ATCGAGACAA  GCACGGTCAA  CTTCCGTACC  GAGCCGCAGG  2640
AACCGCAGGA  GTGGACGGAC  GACCTCGTCC  GTCTGCGGGA  GCGCTATCCC  TGGCTCGTCG  2700
CCGAGGTGGA  CGGCGAGGTC  GCCGGCATCG  CCTACGCGGG  CCCCTGGAAG  GCACGCAACG  2760
CCTACGACTG  GACGGCCGAG  TCGACCGTGT  ACGTCTCCCC  CCGCCACCAG  CGGACGGGAC  2820
TGGGCTCCAC  GCTCTACACC  CACCTGCTGA  AGTCCCTGGA  GGCACAGGGC  TTCAAGAGCG  2880
TGGTCGCTGT  CATCGGGCTG  CCCAACGACC  CGAGCGTGCG  CATGCACGAG  GCGCTCGGAT  2940
ATGCCCCCCG  CGGCATGCTG  CGGGCGGCCG  GCTTCAAGCA  CGGGAACTGG  CATGACGTGG  3000
GTTTCTGGCA  GCTGGACTTC  AGCCTGCCGG  TACCGCCCCG  TCCGGTCCTG  CCCGTCACCG  3060
AGATCTGATC  TCACGCGTCT  AGGATCCGAA  GCAGATCGTT  CAAACATTTG  GCAATAAAGT  3120
TTCTTAAGAT  TGAATCCTGT  TGCCGGTCTT  GCGATGATTA  TCATATAATT  TCTGTTGAAT  3180
TACGTTAAGC  ATGTAATAAT  TAACATGTAA  TGCATGACGT  TATTTATGAG  ATGGGTTTTT  3240
```

| | | | | | |
|---|---|---|---|---|---|
| ATGATTAGAG | TCCCGCAATT | ATACATTTAA | TACGCGATAG | AAAACAAAAT | ATAGCGCGCA | 3300 |
| AACTAGGATA | AATTATCGCG | CGCGGTGTCA | TCTATGTTAC | TAGATCGGGA | AGATCCTCTA | 3360 |
| GAGTCGACCT | GCAGGCATGC | AAGCTTGGCG | TAATCATGGT | CATAGCTGTT | TCCTGTGTGA | 3420 |
| AATTGTTATC | CGCTCACAAT | TCCACACAAC | ATACGAGCCG | GAAGCATAAA | GTGTAAAGCC | 3480 |
| TGGGGTGCCT | AATGAGTGAG | CTAACTCACA | TTAATTGCGT | TGCGCTCACT | GCCCGCTTTC | 3540 |
| CAGTCGGGAA | ACCTGTCGTG | CCAGCTGCAT | TAATGAATCG | GCCAACGCGC | GGGGAGAGGC | 3600 |
| GGTTTGCGTA | TTGGGCGCTC | TTCCGCTTCC | TCGCTCACTG | ACTCGCTGCG | CTCGGTCGTT | 3660 |
| CGGCTGCGGC | GAGCGGTATC | AGCTCACTCA | AAGGCGGTAA | TACGGTTATC | CACAGAATCA | 3720 |
| GGGGATAACG | CAGGAAAGAA | CATGTGAGCA | AAAGGCCAGC | AAAAGGCCAG | GAACCGTAAA | 3780 |
| AAGGCCGCGT | TGCTGGCGTT | TTTCCATAGG | CTCCGCCCCC | CTGACGAGCA | TCACAAAAAT | 3840 |
| CGACGCTCAA | GTCAGAGGTG | GCGAAACCCG | ACAGGACTAT | AAAGATACCA | GGCGTTTCCC | 3900 |
| CCTGGAAGCT | CCCTCGTGCG | CTCTCCTGTT | CCGACCCTGC | CGCTTACCGG | ATACCTGTCC | 3960 |
| GCCTTTCTCC | CTTCGGGAAG | CGTGGCGCTT | TCTCAATGCT | CACGCTGTAG | GTATCTCAGT | 4020 |
| TCGGTGTAGG | TCGTTCGCTC | CAAGCTGGGC | TGTGTGCACG | AACCCCCCGT | TCAGCCCGAC | 4080 |
| CGCTGCGCCT | TATCCGGTAA | CTATCGTCTT | GAGTCCAACC | CGGTAAGACA | CGACTTATCG | 4140 |
| CCACTGGCAG | CAGCCACTGG | TAACAGGATT | AGCAGAGCGA | GGTATGTAGG | CGGTGCTACA | 4200 |
| GAGTTCTTGA | AGTGGTGGCC | TAACTACGGC | TACACTAGAA | GGACAGTATT | TGGTATCTGC | 4260 |
| GCTCTGCTGA | AGCCAGTTAC | CTTCGGAAAA | AGAGTTGGTA | GCTCTTGATC | CGGCAAACAA | 4320 |
| ACCACCGCTG | GTAGCGGTGG | TTTTTTTGTT | TGCAAGCAGC | AGATTACGCG | CAGAAAAAAA | 4380 |
| GGATCTCAAG | AAGATCCTTT | GATCTTTTCT | ACGGGGTCTG | ACGCTCAGTG | GAACGAAAAC | 4440 |
| TCACGTTAAG | GGATTTTGGT | CATGAGATTA | TCAAAAAGGA | TCTTCACCTA | GATCCTTTTA | 4500 |
| AATTAAAAAT | GAAGTTTTAA | ATCAATCTAA | AGTATATATG | AGTAAACTTG | GTCTGACAGT | 4560 |
| TACCAATGCT | TAATCAGTGA | GGCACCTATC | TCAGCGATCT | GTCTATTTCG | TTCATCCATA | 4620 |
| GTTGCCTGAC | TCCCCGTCGT | GTAGATAACT | ACGATACGGG | AGGGCTTACC | ATCTGGCCCC | 4680 |
| AGTGCTGCAA | TGATACCGCG | AGACCCACGC | TCACCGGCTC | CAGATTTATC | AGCAATAAAC | 4740 |
| CAGCCAGCCG | GAAGGGCCGA | GCGCAGAAGT | GGTCCTGCAA | CTTTATCCGC | CTCCATCCAG | 4800 |
| TCTATTAATT | GTTGCCGGGA | AGCTAGAGTA | AGTAGTTCGC | CAGTTAATAG | TTTGCGCAAC | 4860 |
| GTTGTTGCCA | TTGCTACAGG | CATCGTGGTG | TCACGCTCGT | CGTTTGGTAT | GGCTTCATTC | 4920 |
| AGCTCCGGTT | CCCAACGATC | AAGGCGAGTT | ACATGATCCC | CCATGTTGTG | CAAAAAAGCG | 4980 |
| GTTAGCTCCT | TCGGTCCTCC | GATCGTTGTC | AGAAGTAAGT | TGGCCGCAGT | GTTATCACTC | 5040 |
| ATGGTTATGG | CAGCACTGCA | TAATTCTCTT | ACTGTCATGC | CATCCGTAAG | ATGCTTTTCT | 5100 |
| GTGACTGGTG | AGTACTCAAC | CAAGTCATTC | TGAGAATAGT | GTATGCGGCG | ACCGAGTTGC | 5160 |
| TCTTGCCCGG | CGTCAATACG | GGATAATACC | GCGCCACATA | GCAGAACTTT | AAAAGTGCTC | 5220 |
| ATCATTGGAA | AACGTTCTTC | GGGGCGAAAA | CTCTCAAGGA | TCTTACCGCT | GTTGAGATCC | 5280 |
| AGTTCGATGT | AACCCACTCG | TGCACCCAAC | TGATCTTCAG | CATCTTTTAC | TTTCACCAGC | 5340 |
| GTTTCTGGGT | GAGCAAAAAC | AGGAAGGCAA | AATGCCGCAA | AAAAGGGAAT | AAGGGCGACA | 5400 |
| CGGAAATGTT | GAATACTCAT | ACTCTTCCTT | TTTCAATATT | ATTGAAGCAT | TTATCAGGGT | 5460 |
| TATTGTCTCA | TGAGCGGATA | CATATTTGAA | TGTATTTAGA | AAAATAAACA | AATAGGGGTT | 5520 |
| CCGCGCACAT | TTCCCCGAAA | AGTGCCACCT | GACGTCTAAG | AAACCATTAT | TATCATGACA | 5580 |
| TTAACCTATA | AAAATAGGCG | TATCACGAGG | CCCTTTCGTC | | | 5620 |

( 2 ) INFORMATION FOR SEQ ID NO: 4:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
    ( A ) ORGANISM: oligonucleotide MDB80

( i x ) FEATURE:
    ( A ) NAME/KEY: -
    ( B ) LOCATION: 1..21
    ( D ) OTHER INFORMATION: /label=MDB80
         / note= "oligonucleotide designated as MDB80"

( x i ) SEQUENCE DESCRIPTION: SEQ ID NO: 4:

CCGCTTGTCA GTGAATGTTG C                                    21

( 2 ) INFORMATION FOR SEQ ID NO: 5:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
    ( A ) ORGANISM: oligonucleotide MDB81

( i x ) FEATURE:
    ( A ) NAME/KEY: -
    ( B ) LOCATION: 1..21
    ( D ) OTHER INFORMATION: /label=MDB81
         / note= "oligonucleotide designated as MDB81"

( x i ) SEQUENCE DESCRIPTION: SEQ ID NO: 5:

CCGAGGCCAT GGTTGCCGCC G                                    21

( 2 ) INFORMATION FOR SEQ ID NO: 6:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
    ( A ) ORGANISM: oligonucleotide MDB82

( i x ) FEATURE:
    ( A ) NAME/KEY: -
    ( B ) LOCATION: 1..21
    ( D ) OTHER INFORMATION: /label=MDB82
         / note= "oligonucleotide designated as MDB82"

( x i ) SEQUENCE DESCRIPTION: SEQ ID NO: 6:

ACGCATAGGC ATAGGATGAC G                    21

( 2 ) INFORMATION FOR SEQ ID NO: 7:

( i ) SEQUENCE CHARACTERISTICS:
        ( A ) LENGTH: 3627 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Oryza sativa
        ( B ) STRAIN: Akihikari ( i x ) FEATURE:
        ( A ) NAME/KEY: -
        ( B ) LOCATION: 1..2845
        ( D ) OTHER INFORMATION: /label=PT72
            / note= "sequence comprising anther specific
            promoter PT72"

( i x ) FEATURE:
        ( A ) NAME/KEY: -
        ( B ) LOCATION: 2733..2739
        ( D ) OTHER INFORMATION: /label=TATA
            / note= "TATA Box"

( i x ) FEATURE:
        ( A ) NAME/KEY: -
        ( B ) LOCATION: 2765
        ( D ) OTHER INFORMATION: /note= "transcription initiation
            determined by primer extension"

( i x ) FEATURE:
        ( A ) NAME/KEY: -
        ( B ) LOCATION: 2846..2848
        ( D ) OTHER INFORMATION: /label=ATG
            / note= "ATG start of translation of rice T72 gene"

( x i ) SEQUENCE DESCRIPTION: SEQ ID NO: 7:

```
GACAATACAT  CAAGTAAATC  AAACATTACA  AATCAGAACC  TGTCTAAGAA  TCCATCTTAA     60
TTCAGAAAAA  AACTCAGATT  AGATGTTCAT  GCTTCCACCA  GAAGCAGGAA  TGTGCAACCT    120
ACACTTCCTG  TAATTTCCAT  ACTACAATGT  CCCCACTGAC  CACTGTGCCT  GATGCTCTAT    180
TAGAATACCA  CATCCTCCAT  GGCTCCATGT  AAATGCATAT  AAATTTGACT  CTTTAAATTA    240
GTAACTACAA  TTTAAAATTT  ATCGAACATT  GTTCAAATTT  ATAAACAGTT  TCCCCAAATT    300
TAGATGCTCC  CAAATGTACA  CAGCTACTAG  TAAAGCACCA  TCCAGTTTCA  CCTGAACAGG    360
ACTGACATAA  ATGTGTGAAA  AGGGGACGTC  ATTCCCCCAA  ATACAACTGA  ACAATCCTCC    420
ATCAGAACAT  TCATTTGATT  GACATTACTC  GGAGAGATAC  AGCTCGCAGG  CACACGAGAT    480
TCTTCTGCCT  TTCCAATTGC  CACGAACCCA  CATGTCACAC  GACCAACCAA  AAAGAGAGAA    540
TTTTTCTTTG  CACAAACAAA  AAGTGAGATT  TTTTTTTCGC  CACAAAGGTG  CGAACTTTCT    600
TCTCTCTCCC  ACTTTCCAAT  CAAGAAACGA  AGCACTCAAA  CCAAGAACAA  ACCAAGGAAG    660
GAGAGATCGC  TCCCTCTCCC  AGAGCAAACG  AAAGGAGAGA  ACTCAGATGG  ATGCGAACTA    720
CTACCTTGCC  TCTTTCCCCG  GAGAAGCAGC  GAAGGAGAAG  AGCGCGATGC  CGCCGCCGCC    780
GCCGCCTCCG  GCAACCTCCG  GCTCCGGCGA  GTCCGCCTCC  TCCTCCTCTC  TCACCTCTCT    840
CTTCCCAACC  GTGTGGTGTT  CGAGAAGCTT  TTATGCGAGC  GACGTGCAGT  GGAAGCGGTT    900
```

-continued

```
GCTCCCAAGT CAAACTGATG GAGACCACCT ACTATCTTCC TCTTGTTTTC TTCTGCTTTT      960
CTTTTCTTTA TCTTTTTTCT TTCATTTTAT TTTGAGCGAT GAACTTGAGA ACAGTTTGGT     1020
TGTGGGTTAA ATTAAACGGT GCAGAATTGC AAAGCTACGT CCTTTTCGTC TGATTAAGGT     1080
GGTATCAGAA TCCTAATCTG TTAGCTCAGC ATTTGTTTTT GTGTGTTTAA TTGGCCATGA     1140
CATCAGATGG TTCAGACCGG TGGCAGGTCT TCATCGGAGA GGAGAATGAG AGCAATGCAA     1200
GTTGCAAACA ACAAACAGGT CCTTCCAAAC GGGTTGGTTT CATTCCACAG AACAGGATAG     1260
CAACCAGAGC ACAAACCGTT CAACAATATA TATATATATA TATATATA TATATATA         1320
TATATATATA TATATATATG ATTTAAAATT ATATTACTAT TTTAGGATA CGGAACTCTT      1380
AACACATGAA AATCTAAACA TTTTCAACCA ATCAGAACTA CTAGAAAGAT AATCTAACTA     1440
CTTCAAAATT TAAAATTTGA CAAATAAAAT AACTAGTTTT TTCTAAAGCT ATCTTCACTG     1500
GACAACTTAT GAATATTTAT ATTTATGAAG CGAGTACTCT CCTAGTACAT ATTACATATA     1560
TATTCTTCTT CTCATGAAAA ATTAACTTCT CGCTATAAAT CCGAACATAT ATTATGCGTA     1620
GCAAGTTGTT TTTTTAACG GGTGGAGTAA TATTAGAGTA TTTAAATTCC TTCAAATTGC      1680
CATCCCTCTG GGACTTTGCT GCTGTTGTTC TTCCACGGTT GCTGTCAGTG TCACCCAGAT     1740
TTGCATCCTT TCCAGCTCGT AGCTACTGTT CTGCATGTAT TGGACTTGGA TTAAGATCAA     1800
ATGCAGTTGC TATTGTAACT GCACAATAGC AACTGCACAC AATCATGTCC ATTCGTTTTC     1860
AGATCCAACG GCTCTAGATG ACTGCTACAG TACATGCATA ATAGTACATC TCTGCTACAG     1920
TGTTTTGCT GCAGTACCAC TTCATATCCT GGCCTTCCGT TCTAGATCAT GTGATGTACA      1980
TGTTTTTTG AAACAACCCG CACAAGACAT TGATAGAGTA GGAAATGTGA TGTACATGTT      2040
AACGGCTTAA GTTACAGTTA CAATAACAAC TGCACAGGAT CTTGATCCAT GGACTTGTA      2100
TAATATCTCA TCTCGTCGTT CCATTATCGT GGTAACAGTT GGCAACTTGG CATCCAGTGC     2160
TGGAAACTAT GCCGTGTGTA CATCAGGATC GTCCTTTTTG TTCAGTTCCA AGATAGAACA     2220
AGTCCAAAAG ATGGCCGTAG TTTTTTTAGT CACAGTGGAA GCTGACATAG CCGTGGAATA     2280
AGTTCTGCAC AAAAGTTGCC ATTCGAGATC AACTACTGGT AGTAGTAGTC ATCTTCTACC     2340
ACTGCGAATA TTCGAAGGGA CACAAAAAGA TCAACGAGTA AATTAGTTCA CCGGAAGACG     2400
ACACATTATC ACCACAAAAA GACTAAAAAC AAAAAGAAAT TGCCAGGCCA AAAAAGGCAA     2460
AAAAGAAAAA AAAAGATGGC ACGAGGCCCA GGGCTACGGC CCATCTTGTC GCCGGCCCAA     2520
CCGCGCGCGC GAAACGCTCT CGTCGGCTCT CGGCTCGCCG CGACGCGATG GAGAGTTCGC     2580
GCCGCGGCGC GCGCGCGCGT TCGGTGGCTC ACACGCTTGC GCCCTCGTCC TCCGGCCGG      2640
CGCGGGCGCC GACCGCGCGT CCGCCGCATG CGCGCGGCGT AGGTGAGCAA CGCGGGCCTC     2700
GCCGCGCGCG CTCCCCTCCT TCGATCCCCT CCTATAAATC GAGCTCGCGT CGCGTATCGC     2760
CACCACCACC ACGACACACA CGCACGCACC GTGCAGGCAT CGACGACGAG CGAGAGCCCC     2820
TCGGCGGCAG AAGACACTCA CGGCGATGGC GGTGACGAGG ACGGCGCTGC TGGTGGTGTT     2880
GGTAGCGGGG GCGATGACGA TGACGATGCG CGGGGCGGAG GCGCAGCAGC CGAGCTGCGC     2940
GGCGCAGCTC ACGCAGCTGG CGCCGTGCGC GCGAGTCGGC GTGGCGCCGG CGCCGGGGCA     3000
GCCGCTGCCG GCGCCCCGG CGGAGTGCTG CTCGGCGCTG GCGCCGTGT CGCACGACTG       3060
CGCCTGCGGC ACGCTCGACA TCATCAACAG CCTCCCCGCC AAGTGCGGCC TCCGCGCGT      3120
CACCTGCCGT AAGAAAACGA ATAAAATCGA TTTGCTATCT ATCGATGATT GTGTTTTTGT     3180
AGACTAAAACT AAACCCCTAT TAATAATCAA CTAACCGATG AACTGATCGT TGCAGAGTGA    3240
TGGAGATGGT GTGCCAAGGT AATTGCGTTT GCTCGTGCGA GGATGAGAAG AGAAGATTGA     3300
```

| | | | | | |
|---|---|---|---|---|---|
| ATAAGATGTT | TGATGGCAAC | AAGTCATCAG | GCGATCCGAT | CCCTGCAGCT | ATGAATGGGA | 3360 |
| GTATACGTAG | TAGTGGTCTC | GTTAGCATCT | GTGTGTCGCA | TATGCACGCC | GTGCGTGCCG | 3420 |
| TGTCTGTCCT | GCTTGCTCTG | CTGATCGTTC | AATGAACGAC | AAATTAATCT | AACTCTGGAG | 3480 |
| TGACAAGTCG | TTCGAGATAT | ACTAATACTA | CCATGTGCAG | GGTCTTTCAA | CCAAGGTTCA | 3540 |
| TGTTTTCCAC | GAAAGCCGAT | TGAAACGAAA | CCGCGAAATT | TTGATGCGAG | ATGAAAGCAG | 3600 |
| ATTCCGAGTG | AAATTTTAAA | TGGTTTT | | | | 3627 |

(2) INFORMATION FOR SEQ ID NO: 8:

( i ) SEQUENCE CHARACTERISTICS:
        ( A ) LENGTH: 2370 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Oryza sativa
        ( B ) STRAIN: Akihikari ( i x ) FEATURE:
        ( A ) NAME/KEY: -
        ( B ) LOCATION: 1..1808
        ( D ) OTHER INFORMATION: /label=PT42
           / note= "sequence comprising anther specific
           promoter PT42"

( i x ) FEATURE:
        ( A ) NAME/KEY: -
        ( B ) LOCATION: 1748..1755
        ( D ) OTHER INFORMATION: /label=TATA
           / note= "TATA Box"

( i x ) FEATURE:
        ( A ) NAME/KEY: -
        ( B ) LOCATION: 1780
        ( D ) OTHER INFORMATION: /note= "transcription initiation
           site determined by primer extension"

( i x ) FEATURE:
        ( A ) NAME/KEY: -
        ( B ) LOCATION: 1809
        ( D ) OTHER INFORMATION: /label=ATG
           / note= "ATG start of translation of rice T42 gene"

( x i ) SEQUENCE DESCRIPTION: SEQ ID NO: 8:

| | | | | | |
|---|---|---|---|---|---|
| GGCCATCACT | GTCGGGTGCT | GCGCCATGGA | CATCACCGTC | TCCTTCCTGC | GCCGCCGTCG | 60 |
| CCGGTGAGCT | CCAAGGCCGA | AGCCTTCTTC | CCCTCACGCC | ACTACCTCTC | TCTTCCCCAA | 120 |
| TTCCGGCCAA | CGCCGTCCGT | TGCCACAGCG | CCACCTCCAC | GCCATCCCAG | AGCCCCGTGC | 180 |
| CGTGCCACCG | GGTTCGCCTC | CATCTCCTCT | TGCCAACGCC | GACGCTCGTC | GCGGCAGCCA | 240 |
| TGCGCTGTCA | CCGATGAACA | CCGCCGCGCC | ACAGCCATGG | CAGAGCACGG | CCAGGGAGCC | 300 |
| ATGGCTGCTC | TGCCTCCTCC | TCCTTCTCTC | ACATCTGGTT | GCAGCCGGAC | CTAGTCGGCT | 360 |
| TATACAAATG | GCCCATGGGC | AAAATTGTCT | TTTATGAAAG | TTTCTCTCAC | CGTTTCAGTC | 420 |
| GGAAATAATA | AAATAATGGG | AGGATTGTCC | GCCAGCAAAT | TACCATATTT | TTTCGGTGTC | 480 |
| CAAGAGCAAA | TACACGATCT | TCGGGTGTTT | CACAGCAAAG | ACCACAATTT | CTAAGTGTCC | 540 |
| TGTAACAAAT | TTGCCAATA | AAAATTTAAA | ACCAAGGAG | AAGACTGTAC | ATGAAGAAAA | 600 |
| ACAAAGAGAA | TGAAATTACA | TAAGCTCAGG | GGTTATAAAG | TTGATTTATT | TTTAGGATGA | 660 |

```
AGGAAGTGTG  TGAAAACAAT  GGCCAATTGG  GTGTCGGAAA  ATATAACGTG  CTTGCTAAAA    720
TGTCGTCCCC  ATATCCTGTA  GCTGATTATA  GATAGACCCT  GATGGTCAAG  ATGCCCTGTA    780
CTGGATCGTG  TTTCCATGCT  TCATCTCCGC  TTCTCTCAAG  TACTCCCCGA  ACTCACATAT    840
CTGGTGGGCT  GGATCCACAG  TAAGAAACAG  TCAAACAACA  CTCACTTCAT  AGATAACCAA    900
TTGTTTAATT  ATTCTTAGTC  CCTTATCTTA  TACTCCTAGT  AAGTGCTTAA  AAACTTGGTA    960
TAAATATCAA  ATTTATCGTA  CAATTACAAT  ATAATTATAA  CGTATACCAT  GTAATTTTA    1020
AAACTATTTT  TAGATAAAAA  AAATATGGTG  ATGAGCAGCC  GCAGCAGCGG  ACGCCGAACC   1080
ACCTGCCGAA  CATCACCAAG  ATAGCGAGTC  CTAAAATTT   TTAGTGTTCG  TTTGCTGGGT   1140
TGGTAACTAA  TTAAAAAAAA  AGAGCGACTC  ATTAGCTCAT  AAATAATTAC  GTATTAGCTA   1200
ATTTTTTTAA  AAAATAAATT  AATATAACTT  ATAAAGCAGC  TTTTGTATAA  TTTTTTTTT    1260
AAAAAAGTGT  TGTTTAGCAG  TTTTGGGAAG  TGTGCCGAGG  GAAAACGATG  AGATGGGTTG   1320
GGGAAGGAGG  GGGAAGAAGT  GAAGAACACA  GCAAATATAG  GCAGCATCGT  CCCGTACAGA   1380
TCAGGCTGCA  ACCACGCCCC  GCGGAGATAG  TTAACGCGGC  CCACGTTGTG  CTATAGCCCG   1440
TCACTCTCGC  GGGCCTCTCC  AACCTCCAGT  TTTTTTCTA   GCCCATCAGC  TGATACGGGG   1500
CCTTCCCCCC  ATGCAGGAGG  ATGGCCCGCC  ACGCGGTGTT  TTGGGCCGTT  CTCGCCGCGC   1560
GCGCCCGTGC  CGATCCGGGA  CTCATCCCAC  GTGCCGCCTC  GCCACCGCCG  CCGCCGCCGC   1620
TGCTGCTCCG  GCTGCCGGCT  GGACCTTCAC  GCTCACGCGC  TCTCCCTGC   CCAACCACCA   1680
CGCAAACAAA  CACGAAGTTC  GCGCCGTCGA  CCGGCTCCCC  TCCTCCCCG   CGCGCATCGG   1740
ATCCCCCTAC  ATAAACCCTC  TCGCTCGCCA  TCGCCATGGC  AGCAACTCCC  CTCCTCCACT   1800
AGACCACCAT  GCACAGATCG  ATGGCCTCTC  AGGCGGTGGC  GCCCCTCCTC  CTCATCCTCA   1860
TGCTCGCGGC  GGCGGCGGGG  GGCGCGTCGG  CGGCGGTGCA  GTGCGGGCAG  GTGATGCAGC   1920
TGATGGCGCC  GTGCATGCCG  TACCTCGCCG  GCGCCCCGG   GATGACGCCC  TACGGCATCT   1980
GCTGCGACAG  CCTCGGCGTG  CTCAACCGGA  TGGCCCGGC   CCCCGCCGAC  CGCGTCGCCG   2040
TCTGCAACTG  CGTCAAGGAC  GCCGCCGCCG  GCTTCCCCGC  CGTCGACTTC  TCCCGCGCCT   2100
CCGCCCTCCC  CGCCGCCTGC  GGCCTCTCCA  TCAGCTTCAC  CATCGCCCCC  AACATGGACT   2160
GCAACCAGTA  AGTTCATTCA  TTCTTTCTTA  ACTCCAATTC  AATTTATCCA  TCACCTCGAC   2220
TTAAGCCTGA  TTAAACTTAA  CTTGTTCTTT  GCATGCTTGC  ACTATTGCAG  GGTTACAGAG   2280
GAACTGAGAA  TCTGAGAGCG  TGAGGAATCG  AGTTCATGTT  GCATTTATCA  TCAATCATCA   2340
TCGACTAGAT  CAATAAATCG  AGCAAAGCTT                                       2370
```

(2) INFORMATION FOR SEQ ID NO: 9:

( i ) SEQUENCE CHARACTERISTICS:
        ( A ) LENGTH: 2407 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Oryza sativa
        ( B ) STRAIN: Akihikari ( i x ) FEATURE:
        ( A ) NAME/KEY: -
        ( B ) LOCATION: 1..2263

(D) OTHER INFORMATION: /label=PE1
/ note= "sequence comprising anther specific
promoter PE1"

(ix) FEATURE:
(A) NAME/KEY: -
(B) LOCATION: 2181..2187
(D) OTHER INFORMATION: /label=TATA
/ note= "TATA Box"

(ix) FEATURE:
(A) NAME/KEY: -
(B) LOCATION: 2211
(D) OTHER INFORMATION: /note= "transcription initiation
site determined by primer extension"

(ix) FEATURE:
(A) NAME/KEY: -
(B) LOCATION: 2264..2266
(D) OTHER INFORMATION: /label=ATG
/ note= "ATG start of translation of E1 gene"

(xi) SEQUENCE DESCRIPTION: SEQ ID NO: 9:

| | | | | | |
|---|---|---|---|---|---|
| TGATAGTGAC | ATACTCACAT | GCTTTGTCAA | TTCAAGTATC | AGTTCTTTTC | ATATTGATTT | 60 |
| CTTAGTTGAT | GAAAGTATAC | ATATTTCTTG | CCATCAATTC | TTTAGTAGG | TACATTTGGA | 120 |
| CACTAGTGGT | CAGGGTTGAA | CTCTTAACTG | GAGTCTCATC | TGATTTGCTT | ATCTGAGACT | 180 |
| GGGTTTGTGC | AAATCCTGTC | ATGAGGCAAG | GTGGACTGTC | AGTCCATGAC | ACTTTGCTAC | 240 |
| TTCTATTAAG | TTCTCGAAAT | CTTTTCCAGT | GTATGTCCGT | TCTCTTTCAA | ATGAATTATT | 300 |
| TATATGTTCT | GACAGCCTCG | CGGTGTACAT | TTCATTTAAC | TTTTGTCTTC | ACAGGGCCTC | 360 |
| TTGGTATTTT | GTTGAGCAGA | TTGGAATCAA | CCTTCTTGTA | GAACTTCTTG | ATGTCGTCGC | 420 |
| TACCCTTTGC | AACTAGATGG | TCAACTTCTG | TCTTATATCT | TTGGTACAAC | ACTGGCAAAG | 480 |
| TGTGCGCGCA | CAAGAATCCT | GTGAAGTAAG | AAATACAAAC | TTGTCATTGT | GAAAGTTTAG | 540 |
| CTTTATATGA | TCTTGACTCT | AAATTGTTTC | TCCTCAGATC | CTTCTGTGTG | ATTGTTTTAT | 600 |
| TAAAATTTAA | TATTTATCTG | GAATACCTAC | CAATATATAG | TAGACTTGTC | AAGCTGCAAG | 660 |
| AACTTCCAAT | CGCCGACAAT | ACCAATAGAG | ATCCAACCAC | CTTAATATCA | TAAACAATCT | 720 |
| GATTGTTAGT | CCAGAACTAT | ATTGAGTAGT | GAACAACAAT | AGCACATTAA | CATTATGAGG | 780 |
| ATTATTGGCT | AACTCTGCAA | TTCAATATTC | TGATGCGTCT | AATCTGGTCA | ATTTAGCGC | 840 |
| TCCAGAAAGA | ATTGCACAAT | CCTTGGACAA | TGTTGGCACT | GGAACTGTTG | CATGTTTTA | 900 |
| CATCTCTTAT | TAACGTAGCA | AAGGAGTAGA | TTATTATGTA | CCAGGAGAAA | TCTCTTCAGA | 960 |
| TCCTTTCCAC | ATGCAATGTC | GTAAAGAACA | GATACAGTGT | ACGTTAGTTT | GTAATGGACG | 1020 |
| GTCAATGCCA | TTTCTCTGAA | GGCATGTTCA | GAGATGATGA | TTTCTGGGAT | CCTTGGAGGG | 1080 |
| GCCCTGAAAT | TCGGAAACAG | TTAGTTGAGT | TTAGTACCT | AATGTCTTGC | GTTATACTAC | 1140 |
| GTGAAATGCC | ATTTCTGTAA | GCTGAGTTTT | CTACCATCTC | CACAGGAAAT | AAAGCTAATA | 1200 |
| CCTGTCCAAG | AGTGGTGCGG | CATTTGACCA | AATGAAGATC | ACAAGCATGG | CAAGAATGGC | 1260 |
| AATCTGGCAA | AGGAGCGGAA | TTATATTGTA | TTCTACTACA | TCGAACAGGA | ACCATATCAA | 1320 |
| TGTTGCCCCA | GCAAGGACCC | CCGCAGATAA | GTTCCTGTTC | TTCCACAGCA | GAATATCCGC | 1380 |
| AACTGCATAG | CTCCCAACAA | TGAAATCCAA | AACCACATCG | GCTCAGAGAG | AAGTTATGAT | 1440 |
| AAAAGGCACT | AATTCTGAAT | AATTTCCTAG | AAAGCGAATA | ATAATAGCAC | ACCTTGACCT | 1500 |
| CCACCAAGAA | GCTTGTGGAT | CGACTTGTGC | CCATGAAATG | GCATTCTGAC | ATTCTGGTCA | 1560 |
| CTGTCAGAAT | CTCTCGGAAA | ATGAGGAGGC | ATAGCTTCGT | GTGTGTATGT | GTGTGGGATA | 1620 |
| TTACGCTGCT | AAAACTTTGT | GTTTCTGATC | GATCTGGTTA | GAGAGCATCG | TCTTTATAAG | 1680 |

| | | | | | | |
|---|---|---|---|---|---|---|
| CACTTAAAAA | TGGTAGTATA | ATCTCTCAAG | GAGCCTATAC | TGCCAAGGAA | AGGATAGCTT | 1740 |
| GGCCTGTGGG | GATTGAGCCG | TTGAAGGGAA | CAAACGAATA | CAGTTACCTT | ACCAGATGTT | 1800 |
| TGCCACGACA | TGGGCAACGT | CATTGCTAGA | CCAAGAAGGC | AAGAAGCAAA | GTTTAGCTGT | 1860 |
| CAAAAAGAT | ATGCTAGAGG | CTTTCCAGAA | TATGTTCTAT | CTCAGCCAGA | CCAATGGGGG | 1920 |
| CAAAATTTAC | TACTATTTGC | CATACATTAA | CCACGTAAAA | GTCCTACACT | CAACCTAACT | 1980 |
| GTTGAACGGT | CCTGTTCTGG | CCAACGGTGA | GAATGCACCT | AATGGACGGG | ACAACACTTC | 2040 |
| TTTCACCGTG | CTACTGCTAC | ATCCTGTAGA | CGGTGGACGC | GTGAGGTGCT | TTCGCCATGA | 2100 |
| CCGTCCTTGG | TTGTTGCAGT | CACTTGCGCA | CGCTTGCACC | GTGACTCACC | TGCCACATTG | 2160 |
| CCCCCGCCGT | CGCCGGCGCC | TACAAAAGCC | ACACACGCAC | GCCGGCCACG | ATAACCCATC | 2220 |
| CTAGCATCCC | GGTGTCCAGC | AAGAGATCCA | TCAAGCCGTC | GCGATGACGA | CGAGGCCTTC | 2280 |
| TGTTTTTTCC | ACCGTTGTCG | CGGCGATCGC | CATCGCCGCG | CTGCTGAGCA | GCCTCCTCCT | 2340 |
| CCTGCAGGCT | ACCCCGGCCG | CGGCCAGCGC | GAGGGCCTCG | AAGAAGGCTT | CGTGCGACCT | 2400 |
| GATGCAG | | | | | | 2407 |

( 2 ) INFORMATION FOR SEQ ID NO: 10:

( i ) SEQUENCE CHARACTERISTICS:
        ( A ) LENGTH: 2784 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Zea mays ( i x ) FEATURE:
        ( A ) NAME/KEY: -
        ( B ) LOCATION: 1..1179
        ( D ) OTHER INFORMATION: /label=PCA55
           / note= "region comprising the anther specific
           promoter and the leader sequence, PCA55"

( i x ) FEATURE:
        ( A ) NAME/KEY: -
        ( B ) LOCATION: 1072
        ( D ) OTHER INFORMATION: /label=TATA
           / note= "TATA Box"

( i x ) FEATURE:
        ( A ) NAME/KEY: -
        ( B ) LOCATION: 1180..1596
        ( D ) OTHER INFORMATION: /note= "presumed coding sequence of
           corn CA55 gene"

( x i ) SEQUENCE DESCRIPTION: SEQ ID NO: 10:

| | | | | | | |
|---|---|---|---|---|---|---|
| TGGTATGCAT | CAATAGAGCC | GGAAGATGGT | CTGGAGTAAG | GACCTGGCAG | TGTGATACGG | 60 |
| GAACTTGACA | TCTGAATAGA | TATTCTCCCT | TGTCCCTCTG | GTAAAAAAA | CTGTTGTCAC | 120 |
| ATTTGCCTTC | GCTGTGACTT | GGATGTATCA | TGTATATCTT | TGACCATTGA | TATCTTGGTT | 180 |
| AATCAGACGG | TGCATTACAA | TCATGGCCTC | ATTCATATAG | GGTTTAGGGT | TACCACGATT | 240 |
| GGTTTGCATA | AGTAGTACCC | CTCCGTTTCA | AATTATGTCG | TATTTTGATT | TTTTAGATAC | 300 |
| ACTTTTTATA | TAATTTTTTA | TTTTAAATTA | GGTGTTTTAT | ATAATACGTA | TCTAAGTGTA | 360 |
| TAATAAAATA | TATGTATCTA | AAAGCTGTAA | TTTAGTATAA | ATTAGAATGG | TGTATATCTT | 420 |
| CAATGTATGA | CAAATAATTT | GAAATGGAGG | AGGGTATGAA | AAGCCAAAAC | CTCCTAGAAT | 480 |

```
ATGGAATGGA GGGAATACAT ACAAATTCTT TGCTTCAGTT AAAAGAAACG AGAAAAGGAG      540
GGGAATGGGG AATCGTACTT CAGTTTTTAC GAGTTTTCAT CAAACATGTA TGCACGTCTT      600
CCCTTGGTTG ATGCATCTTT TTGGCAAATC TTCGTTTAAT TGCGGCTTCT TTTTTATACC      660
GTTCGAAGGT TTTCGTCGTC AATGCTGAAA CTCCACTTTC ACCACCTTCG GTTGCATCTG      720
CTTGCTTTCA ATTCACCTCT AATTAGTCCA AGTGTTTCAT TGGACGAAGG TCCAAGTCCT      780
TCAGATCATC TCAATTTTCT TTGATCTGAA ACAACAATTT AAAACTGATT TTGTTACCTT      840
GACCTGTCGA AGACCTTCGA ACGAACGGTA CTGTAAAAAT ACTGTACCTC AGATTTGTGA      900
TTTCAATTCG ATTCGGGTCT CCTGGCTGGA TGAAACCAAT GCGAGAGAAG AAGAAAAAAT      960
GTTGCATTAC GCTCACTCGA TCGGTTACGA GCACGTAGTT GGCGCCTGTC ACCCAACCAA     1020
ACCAGTAGTT GAGGCACGCC CTGTTGCTC ACGATCACGA ACGTACAGCA CTATAAAACA     1080
CGCAGGGACT GGAAAGCGAG ATTTCACAGC TCAAAGCAGC CAAAACGCAG AAGCTGCACT     1140
GCATATACAG AAGATACATC GAGCTAACTA GCTGCAGCGA TGTCTCGCTC CTGCTGCGTC     1200
GCCGTGTCGG TGCTTCTCGC TGTCGCCGCG ACAGCCAGCG CCACCGCGCC GGCATGGCTG     1260
CACGAGGAGC AGCACCTCGA GGAGGCCATG GCCACGGGCC CGCTGGTCGC AGAGGGTGCG     1320
AGGGTGGCGC CCTCCGCGTC CACCTGGGCT GCCGACAAGG CGTCGCCGGC GAGGCCGAGC     1380
GGCGGCATGG CCACGCAGGG CGACGACCAG AGCTCGTCGG GCGGCAGTGG CAGCAGCGGT     1440
GAGCACGGCA AGGCGGAGGG CGAGAAGCAG GGCAAGAGCT GCCTCACCAA GGAGGAGTGC     1500
CACAAGAAGA AGATGATCTG TGGCAAGGGC TGCACGCTCT CGGCGCACAG CAAGTGCGCC     1560
GCCAAGTGCA CCAAGTCCTG TGTCCCCACC TGCTAGGAGC CGAGGCCGGA GCTTGCCGGC     1620
GGCGAGACCT CGATCGATCG AGTGCTTCAC TTCACTTCTT TGTTATAGTT CTTGTGTGTT     1680
GCCGTTGCGT TGCGTTGCGT AGACGAAGGG AATAAGGAAG GGTAATTGGA TTACCTGTTC     1740
CAGATCTCTG TGTAAGCGTG TTGTCGTGAC AAGTCTTTTG ATCCAGAGCG AGGGATGGAT     1800
AGATCGCGCT CGCAGTTTTA ATTGCAATGC TAGTTCAATA TGTGTGCATC ATGTTGGCAA     1860
CTACATAGTC CAGATTCAAA CCGAGATCGC TGTTTAGCAT GCCAGCACAA TAATAACGGT     1920
ACAATCATAT TATATTTTAT ACAAATGCAC AATTTATCTC TAGAGATGTC AATGGGAAAT     1980
TCCTCATCGG GTTATATCAT CTCAGACTCA TCCCCATCAT ATTTGATTCA TCCTCATACT     2040
CATCCTCATA TCTATCATGA GTGCAAAACT CATTTCATAC CCATCTCTAT TTGGTTTAG     2100
GGTCTCCATC CCTAATTAAG GGATAACTAG TACTAACAAC TAGCACAAAC TATCTAGATT     2160
TCAGATATCA CCACATTGAC AAACAATCAT CCATGAACTA TGATCCATTC ATCCATCCAT     2220
CAAAAAATAA ATCGGTATTT CGAGAACGAT AGAAGAAATG AAGTCGGCTC ACCTTTCTTG     2280
GTCACCATTT GAGTTTGTTG GTGCCTGAGA ATCCATGGTC GTCATCGTCG TCCTAGGGAT     2340
CGGCGGTGCT CCTCGTTGTT GGTAAAGTCG CCAGTGTGTA GTGCTAGCGC AACTGTCCAG     2400
GCGTGCAACG GTTGGCCGGC TGGAAAGGGC ATAGCGTATG GCTGGTTATT TTAGGGTTT     2460
TGTTTTTTTA CTAATCTGCT AGTTGCCTTG CCATGTTGTC TTATTGGGCT AGGATCTAGG     2520
GCTTGTTACG CTGCTGTGTT GGGCTTGGTG TCCGGTTCAG CCTCAACTCA TTCATACAAA     2580
TCAGATTCAT ACAAAACAGG TATACACGTA TGAAATATCC ATGGATAATC AGGTTCGAAT     2640
TATTGTCCCC TAAACCCATA CACGTTTACC CAATGGATGG ATATTTGTC TCATATCCAT     2700
ACACATGAGA CGATTTTTGT CCCATACCTG TGCTCTAATA GGAGAATTTC TCTCGGGATA     2760
GCGAGTATCG GATCCTCTAG AGTC                                           2784
```

( 2 ) INFORMATION FOR SEQ ID NO: 11:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: oligonucleotide Zm13Oli2

( i x ) FEATURE:
        ( A ) NAME/KEY: -
        ( B ) LOCATION: 1..24
        ( D ) OTHER INFORMATION: /label=Zm13Oli2
             / note= "oligonucleotide designated as Zm13Oli2"

( x i ) SEQUENCE DESCRIPTION: SEQ ID NO: 11:

GTGGATTGAA CGGGACTGAG TTGG                                                        24

( 2 ) INFORMATION FOR SEQ ID NO: 12:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: oligonucleotide Zm13Oli1

( i x ) FEATURE:
        ( A ) NAME/KEY: -
        ( B ) LOCATION: 1..25
        ( D ) OTHER INFORMATION: /label=Zm13Oli1
             / note= "oligonucleotide designated as Zm13Oli1"

( x i ) SEQUENCE DESCRIPTION: SEQ ID NO: 12:

AAGTCTCCAA GACTTTGGTT ATTCC                                            25

( 2 ) INFORMATION FOR SEQ ID NO: 13:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Oligonucleotide Zm13Oli5

( i x ) FEATURE:
        ( A ) NAME/KEY: -
        ( B ) LOCATION: 1..31
        ( D ) OTHER INFORMATION: /label=Zm13Oli5
             / note= "oligonucleotide designated as Zm13Oli5"

( x i ) SEQUENCE DESCRIPTION: SEQ ID NO: 13:

GGATCCATGG TTGCCGCCGG GTGAATGTAC G 31

( 2 ) INFORMATION FOR SEQ ID NO: 14:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: oligonucleotide BXOL2

( i x ) FEATURE:
        ( A ) NAME/KEY: -
        ( B ) LOCATION: 1..24
        ( D ) OTHER INFORMATION: /label=BXOL2
                / note= "oligonucleotide designated as BXOL2"

( x i ) SEQUENCE DESCRIPTION: SEQ ID NO: 14:

ACGGAAAACC TGAAGCACAC TCTC 24

( 2 ) INFORMATION FOR SEQ ID NO: 15:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: oligonucleotide TA29SBXOL2

( i x ) FEATURE:
        ( A ) NAME/KEY: -
        ( B ) LOCATION: 1..49
        ( D ) OTHER INFORMATION: /label=TA29SBXOL2
                / note= "oligonucleotide designated as TA29SBXOL2"

( x i ) SEQUENCE DESCRIPTION: SEQ ID NO: 15:

GTTTTTACTT AAAGAAATTA GCTACCATGA AAAAGCAGT CATTAACGG 49

( 2 ) INFORMATION FOR SEQ ID NO: 16:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: oligonucleotide PTA29OL5

( i x ) FEATURE:
        ( A ) NAME/KEY: -
        ( B ) LOCATION: 1..27

( D ) OTHER INFORMATION: /label=PTA29OL5
/ note= "oligonucleotide designated as PTA29OL5"

( x i ) SEQUENCE DESCRIPTION: SEQ ID NO: 16:

TGGCCATAAC TGAAATCAGG GTGAGAC        27

( 2 ) INFORMATION FOR SEQ ID NO: 17:

( i ) SEQUENCE CHARACTERISTICS:
       ( A ) LENGTH: 4808 base pairs
       ( B ) TYPE: nucleic acid
       ( C ) STRANDEDNESS: double
       ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
       ( A ) ORGANISM: EcoRI-HindIII fragment of plasmid pTS218

( i x ) FEATURE:
       ( A ) NAME/KEY: -
       ( B ) LOCATION: complement (18..401)
       ( D ) OTHER INFORMATION: /label=3'nos
           / note= "3'regulatory sequence containing the
           polyadenylation site derived from Agrobacterium
           T-DNA nopaline synthase gene"

( i x ) FEATURE:
       ( A ) NAME/KEY: -
       ( B ) LOCATION: complement (402..737)
       ( D ) OTHER INFORMATION: /label=barnase
           / note= "coding region of the barnase gene of
           Bacillus amyloliquefaciens"

( i x ) FEATURE:
       ( A ) NAME/KEY: -
       ( B ) LOCATION: complement (738..1944)
       ( D ) OTHER INFORMATION: /label=PZM13
           / note= "promoter region of the Zm13 gene of Zea
           mays"

( i x ) FEATURE:
       ( A ) NAME/KEY: -
       ( B ) LOCATION: complement (1945..2281)
       ( D ) OTHER INFORMATION: /label=3'nos ( i x ) FEATURE:
       ( A ) NAME/KEY: -
       ( B ) LOCATION: complement (2282..2554)
       ( D ) OTHER INFORMATION: /label=barstar
           / note= "coding region of the barstar gene of
           Bacillus amyloliquefaciens"

( i x ) FEATURE:
       ( A ) NAME/KEY: -
       ( B ) LOCATION: complement (2555..3099)
       ( D ) OTHER INFORMATION: /label=PTA29
           / note= "promoter region of the TA29 gene of
           Nicotiana tabacum"

( i x ) FEATURE:
       ( A ) NAME/KEY: -
       ( B ) LOCATION: 3100..3932
       ( D ) OTHER INFORMATION: /label=35S3
           / note= '"35S3"promoter sequence derived from
           cauliflower mosaic virus isolate CabbB-JI"

( i x ) FEATURE:
       ( A ) NAME/KEY: -
       ( B ) LOCATION: 3933..4484
       ( D ) OTHER INFORMATION: /label=bar
           / note= "coding region of the phosphinothricin
           acetyltransferase gene"

( i x ) FEATURE:
    ( A ) NAME/KEY: -
    ( B ) LOCATION: 4485..4763
    ( D ) OTHER INFORMATION: /label=3'nos ( i x ) FEATURE:
    ( A ) NAME/KEY: -
    ( B ) LOCATION: 2333..2356
    ( D ) OTHER INFORMATION: /label=BXOL2
    / note= "region corresponding to oligonucleotide BXOL2"

( i x ) FEATURE:
    ( A ) NAME/KEY: -
    ( B ) LOCATION: complement (2538..2586)
    ( D ) OTHER INFORMATION: /label=TA29SBXOL2
    / note= "region complementary to oligonucleotide TA29SBXOL2"

( i x ) FEATURE:
    ( A ) NAME/KEY: -
    ( B ) LOCATION: complement (2800..2823)
    ( D ) OTHER INFORMATION: /label=PTA29OL5
    / note= "region complementary to part of oligonucleotide PTA29OL5"

( x i ) SEQUENCE DESCRIPTION: SEQ ID NO: 17:

```
GAATTCGAGC TCGGTACCCG GGGATCTTCC CGATCTAGTA ACATAGATGA CACCGCGCGC    60
GATAATTTAT CCTAGTTTGC GCGCTATATT TTGTTTTCTA TCGCGTATTA AATGTATAAT   120
TGCGGGACTC TAATCATAAA AACCCATCTC ATAAATAACG TCATGCATTA CATGTTAATT   180
ATTACATGCT TAACGTAATT CAACAGAAAT TATATGATAA TCATCGCAAG ACCGGCAACA   240
GGATTCAATC TTAAGAAACT TTATTGCCAA ATGTTTGAAC GATCTGCTTC GGATCCTCTA   300
GAGNNNCCG GAAAGTGAAA TTGACCGATC AGAGTTTGAA GAAAAATTTA TTACACACTT   360
TATGTAAAGC TGAAAAAAAC GGCCTCCGCA GGAAGCCGTT TTTTCGTTA TCTGATTTTT    420
GTAAAGGTCT GATAATGGTC CGTTGTTTTG TAAATCAGCC AGTCGCTTGA GTAAAGAATC   480
CGGTCTGAAT TTCTGAAGCC TGATGTATAG TTAATATCCG CTTCACGCCA TGTTCGTCCG   540
CTTTTGCCCG GGAGTTTGCC TTCCCTGTTT GAGAAGATGT CTCCGCCGAT GCTTTCCCC    600
GGAGCGACGT CTGCAAGGTT CCCTTTTGAT GCCACCAGC CGAGGGCTTG TGCTTCTGAT    660
TTTGTAATGT AATTATCAGG TAGCTTATGA TATGTCTGAA GATAATCCGC AACCCCGTCA   720
AACGTGTTGA TAACCGGTAC CATGGTTGCC GCCGGGTGAA TGTACGTGTT TTCCCCTCCC   780
CCCTTGTGGA TGTCGGAGGA AAAGGGCGGG ACCTTCCTT ATTATTTGTG TGAGGGAGGG    840
AGGGTGAGAC GAGGGTGGCA AATCTGGCCT GGTTTCGTAA CGCAGCCTGT GGTGTCCTTA   900
AATAATCTGC GAGACCCGAA GATTTGTCTG GCTGCCCGTA GAAATAGTGG CCGACGGCCA   960
GAAAGCCGTT TTGACCTAGT TTTGTGGCAT GGGGAGGTGA AAAATATGTC GAATTTGGTT  1020
GAGTTTTTCA GCGGTCCACA AAAGTTGGAT TTGCGACTTC TAATCTTCTA TGCTGCTATG  1080
TAAAACTAAA TAAGACGCGC TCAACAAAAC GGTATCAGTT AAATGTATCC ATAAGTGAAT  1140
AGTATATAGA ATCACTAAAT GGCAGCTTCT CATATTTAGC ATAGTACTTG GACAAATGTC  1200
ACGCAAGATG TATTATAAAA ACACATCGGT GTTGAGTGTT GATACAATAA AATCTCAATA  1260
GTTGTTTTAA TCTCAATCCA TGTGGATTGA ACGGGACTGA GTTGGTTTAA ATCCCTAGTA  1320
AGTCAAAATT ATTTCTAATT TTATCTAAAT CTCATCTAAT CCACGTGGAA TAGGAATAAC  1380
CAAACTGTTG GAGACTTGTT CTCAAGTGCT ATGAGTTAAG AACAAGGCAA CATAGAAAAT  1440
ATTAATCGTT AAGGTCCTTC GTCCTTCGAA GCATTATTTC CCTTAGGATA TAATGGTTTA  1500
CGGACGAAGG TTATGAAGGA CGTACCTTCA TAAATTCATT AAACAATGAC GAAGGATGAA  1560
```

| | | | | | |
|---|---|---|---|---|---|
| ATATAAGAA | TATAAAAGAC | AACATGAACA | ATTATATATT | ATTATTAGGT | ACAAACAGAA | 1620
| ATATCGTTGA | ATTACAAGTG | TACCTTCAAT | AGGAATGAGA | TGACAGTACA | AGCGTGACGC | 1680
| AAAAAGCGAA | TGCCAAGTCA | GCGTGAACAG | TACGGGAATA | CTGTTCACCT | ATTTATAGGC | 1740
| ACGGGACGTA | GCCTGTGCAA | AATTACATTA | ATGCCCTTTA | CACTTAATAA | TAAACCTATA | 1800
| GTAATCTGTT | GAGGTCTAAA | TAGCCTTTTC | ATCTTTAAGT | CGGTTTCAAC | TGCTGCTGTC | 1860
| TTGCCGAAGC | TTTCCTGCTT | ACACCTTAGG | CGCTTCACCA | ACCTTCGTAT | TATTCTGGTC | 1920
| TACTGTGATG | CCTGACTTGA | GTCCGAAGAT | GGGGATCTTC | CCGATCTAGT | AACATAGATG | 1980
| ACACCGCGCG | CGATAATTTA | TCCTAGTTTG | CGCGCTATAT | TTTGTTTTCT | ATCGCGTATT | 2040
| AAATGTATAA | TTGCGGGACT | CTAATCATAA | AAACCCATCT | CATAAATAAC | GTCATGCATT | 2100
| ACATGTTAAT | TATTACATGC | TTAACGTAAT | TCAACAGAAA | TTATATGATA | ATCATCGCAA | 2160
| GACCGGCAAC | AGGATTCAAT | CTTAAGAAAC | TTTATTGCCA | AATGTTGAA | CGATCTGCTT | 2220
| CGGATCCTCT | AGACCAAGCT | AGCTTGCGGG | TTTGTGTTTC | CATATTGTTC | ATCTCCCATT | 2280
| GATCGTATTA | AGAAAGTATG | ATGGTGATGT | CGCAGCCTTC | CGCTTTCGCT | TCACGGAAAA | 2340
| CCTGAAGCAC | ACTCTCGGCG | CCATTTTCAG | TCAGCTGCTT | GCTTGTTCA | AACTGCCTCC | 2400
| ATTCCAAAAC | GAGCGGGTAC | TCCACCCATC | CGGTCAGACA | ATCCCATAAA | GCGTCCAGGT | 2460
| TTTCACCGTA | GTATTCCGGA | AGGGCAAGCT | CCTTTTTCAA | TGTCTGGTGG | AGGTCGCTGA | 2520
| TACTTCTGAT | TTGTTCCCCG | TTAATGACTG | CTTTTTTCAT | GGTAGCTAAT | TTCTTTAAGT | 2580
| AAAAACTTTG | ATTTGAGTGA | TGATGTTGTA | CTGTTACACT | TGCACCACAA | GGGCATATAT | 2640
| AGAGCACAAG | ACATACACAA | CAACTTGCAA | AACTAACTTT | TGTTGGAGCA | TTTCGAGGAA | 2700
| AATGGGGAGT | AGCAGGCTAA | TCTGAGGGTA | ACATTAAGGT | TTCATGTATT | AATTTGTTGC | 2760
| AAACATGGAC | TTAGTGTGAG | GAAAAAGTAC | CAAAATTTTG | TCTCACCCTG | ATTTCAGTTA | 2820
| TGGAAATTAC | ATTATGAAGC | TGTGCTAGAG | AAGATGTTTA | TTCTAGTCCA | GCCACCCACC | 2880
| TTATGCAAGT | CTGCTTTTAG | CTTGATTCAA | AAACTGATTT | AATTTACATT | GCTAAATGTG | 2940
| CATACTTCGA | GCCTATGTCG | CTTTAATTCG | AGTAGGATGT | ATATATTAGT | ACATAAAAAA | 3000
| TCATGTTTGA | ATCATCTTTC | ATAAAGTGAC | AAGTCAATTG | TCCCTTCTTG | TTTGGCACTA | 3060
| TATTCAATCT | GTTAATGCAA | ATTATCCAGT | TATACTTAGC | TAGATCCTAC | GCAGCAGGTC | 3120
| TCATCAAGAC | GATCTACCCG | AGTAACAATC | TCCAGGAGAT | CAAATACCTT | CCCAAGAAGG | 3180
| TTAAAGATGC | AGTCAAAAGA | TTCAGGACTA | ATTGCATCAA | GAACACAGAG | AAAGACATAT | 3240
| TTCTCAAGAT | CAGAAGTACT | ATTCCAGTAT | GGACGATTCA | AGGCTTGCTT | CATAAACCAA | 3300
| GGCAAGTAAT | AGAGATTGGA | GTCTCTAAAA | AGGTAGTTCC | TACTGAATCT | AAGGCCATGC | 3360
| ATGGAGTCTA | AGATTCAAAT | CGAGGATCTA | ACAGAACTCG | CCGTGAAGAC | TGGCGAACAG | 3420
| TTCATACAGA | GTCTTTTACG | ACTCAATGAC | AAGAAGAAAA | TCTTCGTCAA | CATGGTGGAG | 3480
| CACGACACTC | TGGTCTACTC | CAAAAATGTC | AAAGATACAG | TCTCAGAAGA | CCAAAGGGCT | 3540
| ATTGAGACTT | TTCAACAAAG | GATAATTTCG | GGAAACCTCC | TCGGATTCCA | TTGCCCAGCT | 3600
| ATCTGTCACT | TCATCGAAAG | GACAGTAGAA | AAGGAAGGTG | GCTCCTACAA | ATGCCATCAT | 3660
| TGCGATAAAG | GAAAGGCTAT | CATTCAAGAT | GCCTCTGCCG | ACAGTGGTCC | CAAAGATGGA | 3720
| CCCCCACCCA | CGAGGAGCAT | CGTGGAAAAA | GAAGACGTTC | CAACCACGTC | TTCAAAGCAA | 3780
| GTGGATTGAT | GTGACATCTC | CACTGACGTA | AGGGATGACG | CACAATCCCA | CTATCCTTCG | 3840
| CAAGACCCTT | CCTCTATATA | AGGAAGTTCA | TTTCATTTGG | AGAGGACACG | CTGAAATCAC | 3900
| CAGTCTCTCT | CTATAAATCT | ATCTCTCTCT | CTATAACCAT | GGACCCAGAA | CGACGCCCGG | 3960

```
CCGACATCCG CCGTGCCACC GAGGCGGACA TGCCGGCGGT CTGCACCATC GTCAACCACT    4020

ACATCGAGAC AAGCACGGTC AACTTCCGTA CCGAGCCGCA GGAACCGCAG GAGTGGACGG    4080

ACGACCTCGT CCGTCTGCGG GAGCGCTATC CCTGGCTCGT CGCCGAGGTG GACGGCGAGG    4140

TCGCCGGCAT CGCCTACGCG GGCCCCTGGA AGGCACGCAA CGCCTACGAC TGGACGGCCG    4200

AGTCGACCGT GTACGTCTCC CCCCGCCACC AGCGGACGGG ACTGGGCTCC ACGCTCTACA    4260

CCCACCTGCT GAAGTCCCTG GAGGCACAGG GCTTCAAGAG CGTGGTCGCT GTCATCGGGC    4320

TGCCCAACGA CCCGAGCGTG CGCATGCACG AGGCGCTCGG ATATGCCCCC CGCGGCATGC    4380

TGCGGGCGGC CGGCTTCAAG CACGGGAACT GGCATGACGT GGGTTTCTGG CAGCTGGACT    4440

TCAGCCTGCC GGTACCGCCC CGTCCGGTCC TGCCCGTCAC CGAGATCTGA TCTCACGCGT    4500

CTAGGATCCG AAGCAGATCG TTCAAACATT TGGCAATAAA GTTTCTTAAG ATTGAATCCT    4560

GTTGCCGGTC TTGCGATGAT TATCATATAA TTTCTGTTGA ATTACGTTAA GCATGTAATA    4620

ATTAACATGT AATGCATGAC GTTATTTATG AGATGGGTTT TTATGATTAG AGTCCCGCAA    4680

TTATACATTT AATACGCGAT AGAAACAAA ATATAGCGCG CAAACTAGGA TAAATTATCG     4740

CGCGCGGTGT CATCTATGTT ACTAGATCGG GAAGATCCTC TAGAGTCGAC CTGCAGGCAT    4800

GCAAGCTT                                                            4808
```

TABLE 1

1. Action: Transform corn embryos (e.g. H99) with male-sterility gene S, linked to herbicide resistance gene bar (Example 5)
   Result: transformed plants with genotype S/s 2. Action: Transform corn embryos (e.g. H99) with fertility-restorer gene R (Example 6)
   Result: transformed plants with genotype R/r 3. Action: Transform corn embryos (e.g; H99) with maintainer gene P (Example 3)
   Result: transformed plants with genotype P/p 4. Action: Cross S/s, r/r × s/s, R/r.
   Select offspring for presence of both S and R genes by means of PCR.
   Result: plants with genotype S/s, R/r 5. Action: Self selected plants of 4 (optional)
   Result: Progeny plants with 9 different genotypes

| gamete ♀ ♂→ ↓ | S, R | S, r | s, R | s, r |
|---|---|---|---|---|
| S, R | S/S, R/R | S/S, R/r | S/s, R/R | S/s, R/r |
| S, r | S/S, R/r | S/S, r/r** | S/s, R/r | S/s, r/r** |
| s, R | S/s, R/R | S/s, R/r | s/s, R/P | s/s, R/r |
| s, r | S/s, R/r | S/s, r/r** | s/s, R/r | s/s, r/r |

**male-sterile plants

TABLE 1-continued

6. Action: self male-fertile progeny plants of 5 (Optional)
   Result:
   6.1. Self of S/S, R/R: 100% male-fertile plants
        Self of S/s, R/R: 100% male-fertile plants
        Self of s/s, R/R: 100% male-fertile plants
        Self of s/s, R/r: 100% male-fertile plants
        Self of s/s, r/r: 100% male-fertile plants 6.2 Self of S/s, R/r: Same progeny as in 5
                         13/16 male-fertile plants
                         with 4/13 herbicide
                         sensitive 6.3 Self of S/S, R/r: Progeny as follows:

| gamete ♀ ♂→ ↓ | S, R | S, r |
|---|---|---|
| S, R | S/S, R/R | S/S, R/r |
| S, r | S/S, R/r | S/S, r/r** |

**male-sterile plants

Thus: 3/4 male-fertile plants, 0% herbicide sensitive
All male-sterile plants are of genotype S/S, r/r 7. Action: Cross
   ♀: P/p (from 3) × ♂: S/s, R/r (from 4)
   this equals in fact
   ♀: s/s, r/r, P/p × ♂: S/s, R/r, p/p
   Result: Progeny with the following genotypes

| gamete ♀ ♂→ ↓ | S, R, p | S, r, p | s, R, p | s, r, p |
|---|---|---|---|---|
| s, r, P | S/s, R/r, P/p | S/s, r/r, P/p | s/s, R/r, P/p | s/s, r/r, P/p |
| s, r, P | S/s, R/r, p/p | S/s, r/r, p/p | s/s, R/r, p/p | s/s, r/r, p/p |

TABLE 1-continued

8. Action: From offspring of 7, select plants with genotype
   S/s, r/r, P/p by screening, by means of PCR and/or Southern
   blotting, for presence of S and P gene and absence of R gene.
   Result: plants with genotype S/s, P/p 9. Action: Self plants with genotype S/s, P/p (from 8)
   Result: progeny with the following genotypes

| gamete ♀ ♂→ ↓ | S, P | S, p | s, P | s, p |
|---|---|---|---|---|
| S, P | S/S, P/P | S/S, P/p | S/s, P/P | S/s, P/p |
| S, p | S/S, P/p | S/S, p/p** | S/s, P/p | S/s, p/p** |
| s, P | S/s, P/P | S/s, P/P | s/s, P/P | s/s, P/p |
| s, p | S/s, P/p | S/s, p/p** | s/s, P/p | s/s, p/p |

**male-sterile plants
Shaded genotypes cannot develop because male
gametes (pollen) are killed off by expression of
the maintainer gene P.

10. Action: self male fertile plants of 9.
    Result
    10.1. Self of s/s, P/p: 100% male-fertile plants
          Self of s/s, p/p: 100% male-fertile plants 10.2  Self of S/s, P/p:  Same progeny as in 9
                             5/8 male-fertile plants with
                             2/5 herbicide sensitive 10.3  Self of S/S, P/p:  Progeny as follows:

| gamete ♀ ♂→ ↓ | S, P | S, p |
|---|---|---|
| S, P | S/S, P/P | S/S, P/p |
| S, p | S/S, P/p | S/S, p/p** |

**male-sterile plants
Shaded genotypes cannot develop because male
gametes (pollen) are killed off by
expression of the maintainer gene P.

FINAL RESULT

- 1/2 male-fertile plants, 0% herbicide sensitive. All
these plants are maintainer plants
- 1/2 male sterile plants. All homozygous for the male-
sterility gene S.

We claim:

1. A process for maintaining a male-sterile line of a plant species, said process comprising:
   1) crossing:
      a) a male-sterile line to be maintained comprising male-sterile parent plants which comprise at a first genetic locus a males-sterility gene comprising a sterility DNA encoding a ribonuclease under the control of sterility promoter which directs expression selectively in specific stamen cells of said plants, wherein said male-sterility gene is homozygous at said first genetic locus; with
      b) a maintainer line comprising male-fertile parent plants which comprise said homozygous male-sterility gene at said first genetic locus, and which further comprise, at a second genetic locus which segregates independently from said first genetic locus, a foreign DNA comprising:
         (i) a restorer gene comprising a restorer DNA encoding a protein that inhibits or prevents the activity of said ribonuclease under the control of a restorer promoter which directs expression at least in said specific stamen cells; and,
         (ii) a pollen-lethality gene comprising, under the control of a first promoter that directs expression selectively in microspores and/or pollen cells of said male-fertile parent plants, a first DNA encoding a first protein or polypeptide which, when produced in a microspore or pollen cell of said male-fertile parent plant, significantly disrupts the metabolism, functioning or development of said microspore or pollen cell;
   wherein said foreign DNA is heterozygous at said second genetic locus; and
   2) harvesting seeds from said male-sterile parent plants, said seeds being capable of growing into a new generation of male-sterile parent plants.

2. The process of claim 1 in which said first DNA encodes a ribonuclease.

3. The process of claim 2 in which said first DNA encodes barnase.

4. The process of claim 1 in which said first promoter is the promoter of the zm13 gene from maize.

5. The process of claim 1 in which said male-sterility gene comprises a sterility DNA encoding barnase, and in which said restorer gene at said second genetic locus in said male-fertile parent plants comprises a restorer DNA encoding barstar.

6. The process of claim 1 in which said sterility promoter directs expression in tapetum cells.

7. The process of claim 1 in which said sterility promoter is selected from the group consisting of the TA29 promoter and the CA55 promoter.

8. The process of claim 1 in which said restorer promoter is identical to said sterility promoter.

9. The process of claim 8 in which said restorer promoter is selected from the group consisting of the TA29 promoter and the CA55 promoter.

10. The process of any one of claims 1 to 4 in which said plant species is maize.

11. The process of claim 5 in which said plant species is maize.

12. A male-fertile parent plant for use in maintaining a male-sterile line of a plant species comprising male-sterile parent plants which comprise at a first genetic locus a male-sterility gene comprising a sterility DNA encoding a ribonuclease under the control of a sterility promoter which directs expression selectively in specific stamen cells of said plants, wherein said male-sterility gene is homozygous at said first genetic locus, wherein said male-fertile parent plant comprises said homozygous male-sterility gene at said first genetic locus and further comprises, at a second genetic locus which segregates independently from said first genetic locus, a foreign DNA comprising:
   I) a restorer gene comprising a restorer DNA encoding a protein that inhibits or prevents the activity of said ribonuclease under the control of a restorer promoter which directs expression at least in said specific stamen cells; and,
   II) a pollen-lethality gene comprising, under the control of a first promoter that directs expression selectively in microspores and/or pollen cells of said male-fertile parent plant, a first DNA encoding a first protein or polypeptide which when produced in a microspore or pollen cell of said male-fertile parent plant significantly disrupts the metabolism, functioning or development of said microspore or pollen cell;

wherein said foreign DNA is heterozygous at said second genetic locus, and wherein said male-fertile parent plant can be crossed to said male-sterile parent plants to produce, on said male-sterile parent plants, only seeds which are capable of growing into a new generation of male-sterile parent plants.

13. The plant of claim 12 in which said first DNA encodes a ribonuclease.

14. The plant of claim 13 in which said first DNA encodes barnase.

15. The plant of claim 12 in which said first promoter is the promoter of the zm13 gene from maize.

16. The plant of claim 12 in which said male-sterility gene comprises a sterility DNA encoding barnase and in which said restorer gene at said second genetic locus in said male-fertile parent plants comprises a restorer DNA encoding barstar.

17. The plant of claim 12 in which said sterility promoter directs expression in tapetum cells.

18. The plant of claim 12 in which said sterility promoter is selected from the group consisting of the TA29 promoter and the CA55 promoter.

19. The plant of claim 12 in which said restorer promoter is identical to said sterility promoter.

20. The plant of claim 19 in which said restorer promoter is selected from the group consisting of the TA29 promoter and the CA55 promoter.

21. The plant of any one of claims 12 to 15 in which said plant species is maize.

22. The plant of claim 16 in which said plant species is maize.

23. A kit for maintaining a male-sterile line of a plant species, said kit comprising:

a) a male-sterile line comprising male-sterile parent plants which comprise at a first genetic locus a male-sterility gene comprising a sterility DNA encoding a ribonuclease under the control of a sterility promoter which directs expression selectively in specific stamen cells of said plants, wherein said male-sterility gene is homozygous at said first genetic locus; and, b) a maintainer line comprising male-fertile parent plants which comprise said homozygous male-sterility gene at said first genetic locus, and which further comprise, at a second genetic locus which segregates independently from said first genetic locus, a foreign DNA comprising:

I) a restorer gene comprising a restorer DNA encoding a protein that inhibits or prevents the activity of said ribonuclease under the control of a restorer promoter which directs expression at least in said specific stamen cells, and, II) a pollen-lethality gene comprising, under the control of a first promoter that directs expression selectively in microspores and/or pollen cells of said male-fertile parent plants, a first DNA encoding a first protein or polypeptide which, when produced in a microspore or pollen cell of said male-fertile parent plant significantly disrupts the metabolism, functioning or development of said microspore or pollen cell, wherein said foreign DNA is heterozygous at said second genetic locus; and wherein said male-sterile and male-fertile parent plants can be crossed to produce, on said male-sterile parent plants, only seeds which are capable of growing into a new generation of male-sterile parent plants.

24. The kit of claim 23 in which said first DNA encodes a ribonuclease.

25. The kit of claim 24 in which said first DNA encodes barnase.

26. The kit of claim 23 in which said first promoter is the promoter of the zm13 gene from maize.

27. The kit of claim 23 in which said male-sterility gene comprises a sterility DNA encoding barnase, and in which said restorer gene at said second genetic locus in said male-fertile parent plants comprises a restorer DNA encoding barstar.

28. The kit of claim 23 in which said sterility promoter directs expression in tapetum cells.

29. The kit of claim 23 in which said sterility promoter is selected from the group consisting of the TA29 promoter and the CA55 promoter.

30. The kit of claim 23 in which said restorer promoter is identical to said sterility promoter.

31. The kit of claim 30 in which said restorer promoter is selected from the group consisting of the TA29 promoter and the CA55 promoter.

32. The kit of any one of claims 23 to 26 in which said plant species is maize.

33. The kit of claim 27 in which said plant species is maize.

* * * * *

UNITED STATES PATENT AND TRADEMARK OFFICE
CERTIFICATE OF CORRECTION

Page 1 of 3

PATENT NO. : 5,750,867
DATED : May 12, 1998
INVENTOR(S) : Mark WILLIAMS and Jan LEEMANS It is certified that error appears in the above-indentified patent and that said Letters Patent is hereby corrected as shown below:

Column 2, line 12, replace "amyloliguefaciens" with --amyloliquefaciens--; and
line 14, replace "amyloliguefaciens" with --amyloliquefaciens--.

Column 3, lines 63 to 64, after "pollen" insert --specific--.

Column 6, line 48, replace "amyloliguefaciens" with --amyloliquefaciens--.

Column 7, line 34, replace "Mol.Gen.Genet." with --Mol. Gen. Genet.--.

Column 8, line 26, replace "Promoter" with --promoter--;
line 27, replace "Promoter" with --promoter--; and
line 28, replace "Promoter" with --promoter--.

Column 9, line 7, replace "BY" with --By--;
line 39, replace "describe" with --described--; and
line 46, after "and" (second occurrence) please replace "p" with --P--.

UNITED STATES PATENT AND TRADEMARK OFFICE
CERTIFICATE OF CORRECTION

PATENT NO. : 5,750,867
DATED : May 12, 1998
INVENTOR(S) : Mark WILLIAMS and Jan LEEMANS It is certified that error appears in the above-indentified patent and that said Letters Patent is hereby corrected as shown below:

Column 11, line 15, replace "P/p" with --$^{P/P}$(superscript)--; and
line 23, replace "P/p" with --$^{P/P}$(superscript)--.

Column 14, line 53, please replace "J.Mol.Biol." with --J. Mol. Biol.--.

Column 15, line 43, replace "pTS18 2carrying" with --pTS182 carrying--; and
line 47, replace "pTS102" with --pTS210--.

Column 17, line 14, replace "form" with --from--; and
line 33, replace "on" with --in--.

Column 18, line 17, replace "phosphinothricine" with --phosphinothricin--.

Column 19, line 10, replace "mag/I" with --mg/I--.

Column 20, line 46, replace "H99$^{s/s,r/r,p/p}$" with --H99$^{S/s,r/r,p/P}$--;
line 53, replace "H99$_{s/s,r/r}$ and H99$_{s/s,r/r}$" with --H99$^{S/S,r/r}$ and H99$^{S/s,r/r}$--; and
line 64, replace "H99$_{s/s,R/r}$" with --H99$^{S/S,R/r}$--.

Column 21, line 2, replace "H99$_{s/s,r/r}$" with --H99$^{S/S,r/r}$--.

UNITED STATES PATENT AND TRADEMARK OFFICE
CERTIFICATE OF CORRECTION

PATENT NO. :   5,750,867
DATED      :   May 12, 1998
INVENTOR(S) :  Mark WILLIAMS and Jan LEEMANS It is certified that error appears in the above-indentified patent and that said Letters Patent is hereby corrected as shown below:

Claim 1,   line 6, replace "males-sterility" with --male-sterility--;
           line 8, before "sterility" insert --a--; and
           line 29, replace "plant" with --plants--.

Claim 16,  line 4, replace "plants" with --plant--.

Claim 23,  line 27, replace "plants" with --plant--.

Signed and Sealed this

Twenty-fourth Day of August, 1999

Attest:

Q. TODD DICKINSON

*Attesting Officer*    *Acting Commissioner of Patents and Trademarks*